(12) United States Patent
Nishi et al.

(10) Patent No.: US 10,789,748 B2
(45) Date of Patent: Sep. 29, 2020

(54) IMAGE PROCESSING DEVICE, IMAGE PROCESSING METHOD, AND NON-TRANSITORY COMPUTER-READABLE RECORDING MEDIUM STORING IMAGE PROCESSING PROGRAM

(71) Applicant: Panasonic Intellectual Property Management Co., Ltd., Osaka (JP)

(72) Inventors: Chie Nishi, Kanagawa (JP); Rieko Asai, Osaka (JP); Sachiko Takeshita, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/384,992

(22) Filed: Apr. 16, 2019

(65) Prior Publication Data

US 2019/0244408 A1 Aug. 8, 2019

Related U.S. Application Data

(63) Continuation of application No. PCT/JP2017/036744, filed on Oct. 11, 2017.

(30) Foreign Application Priority Data

Oct. 24, 2016 (JP) ................................. 2016-207910

(51) Int. Cl.
*G06T 7/60* (2017.01)
*G06T 11/60* (2006.01)
(Continued)

(52) U.S. Cl.
CPC .............. *G06T 11/60* (2013.01); *A45D 44/00* (2013.01); *A45D 44/005* (2013.01);
(Continued)

(58) Field of Classification Search
None
See application file for complete search history.

(56) References Cited

U.S. PATENT DOCUMENTS

| 6,502,583 | B1 | 1/2003 | Utsugi |
| 2003/0062058 | A1 | 4/2003 | Utsugi |

(Continued)

FOREIGN PATENT DOCUMENTS

| EP | 2615576 A1 | 7/2013 |
| EP | 2976963 A1 | 1/2016 |

(Continued)

OTHER PUBLICATIONS

International Search Report of PCT application No. PCT/JP2017/036744 dated Jan. 23, 2018.
(Continued)

*Primary Examiner* — Nicholas R Wilson
(74) *Attorney, Agent, or Firm* — Greenblum & Bernstein, P.L.C.

(57) ABSTRACT

An image processing device includes: an image input unit that inputs a facial image from a predetermined device; an image analyzing unit that calculates one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image; and an image generating unit that decides a superimposing region of a makeup parts image based on one of the facial shape, the proportion lines, and the blocking lines, and generates a simulation image where the makeup parts image has been superimposed on the superimposing region.

12 Claims, 15 Drawing Sheets

(51) Int. Cl.
  *G16H 20/70*   (2018.01)
  *G06T 1/00*    (2006.01)
  *A45D 44/00*   (2006.01)
  *G06T 7/50*    (2017.01)
  *G06K 9/00*    (2006.01)
  *G06T 3/20*    (2006.01)

(52) U.S. Cl.
  CPC ..... *G06K 9/00248* (2013.01); *G06K 9/00268* (2013.01); *G06T 1/00* (2013.01); *G06T 3/20* (2013.01); *G06T 7/50* (2017.01); *G06T 7/60* (2013.01); *G16H 20/70* (2018.01); *G06T 2207/20021* (2013.01); *G06T 2207/30201* (2013.01)

(56) References Cited

U.S. PATENT DOCUMENTS

| | | |
|---|---|---|
| 2006/0132506 A1 | 6/2006 | Utsugi |
| 2012/0223956 A1 | 9/2012 | Saito et al. |
| 2015/0118655 A1* | 4/2015 | Yamanashi ........ G06K 9/00261 434/100 |
| 2016/0125227 A1 | 5/2016 | Soare et al. |

FOREIGN PATENT DOCUMENTS

| | | |
|---|---|---|
| JP | 2010-092439 | 4/2010 |
| JP | 2016-081075 | 5/2016 |
| WO | 1998/039735 | 9/1998 |
| WO | 2008/102440 | 8/2008 |

OTHER PUBLICATIONS

"Blush application for a small-face look Per face type", May 15, 2014, pp. 1-3, Internet <URL:https://moteco-web.jp/beauty/13089>.

"Easy and beautiful ! How to make adult natural makeup (How to put in Cheek)", Aug. 10, 2016, pp. 16-19, Internet <URL:https://dress-r.net/check/3464>.

The Extended European Search Report dated Sep. 27, 2019 for the related European Patent Application No. 17865732.6.

* cited by examiner

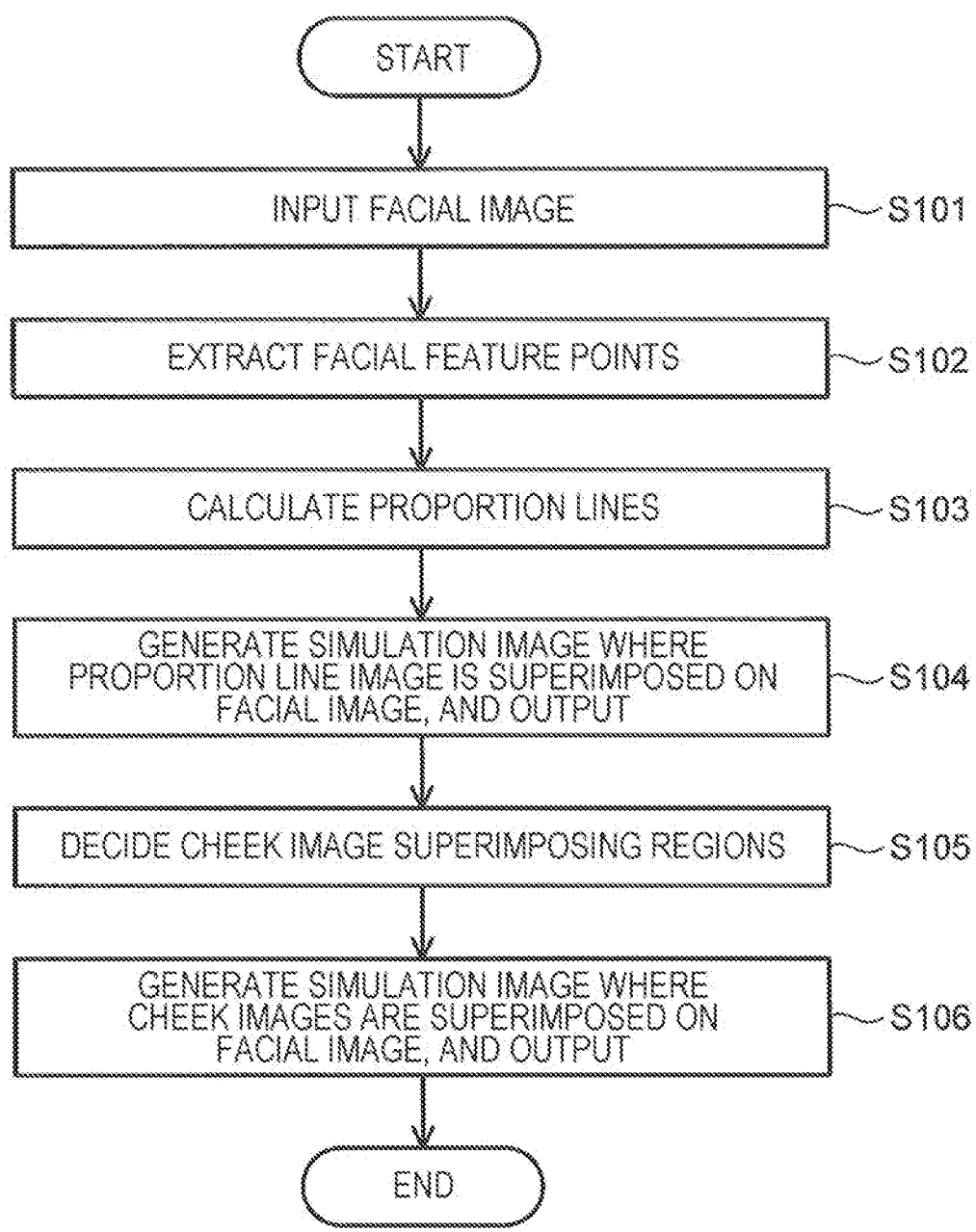

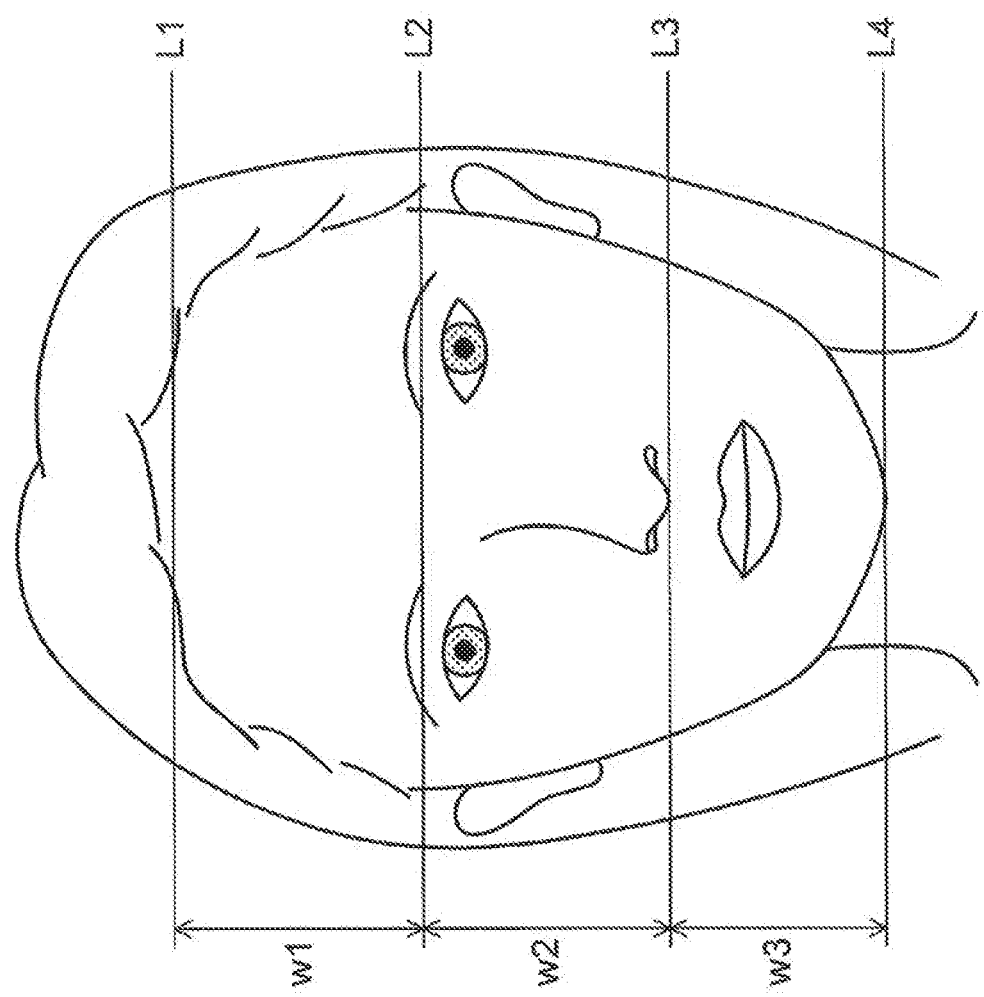

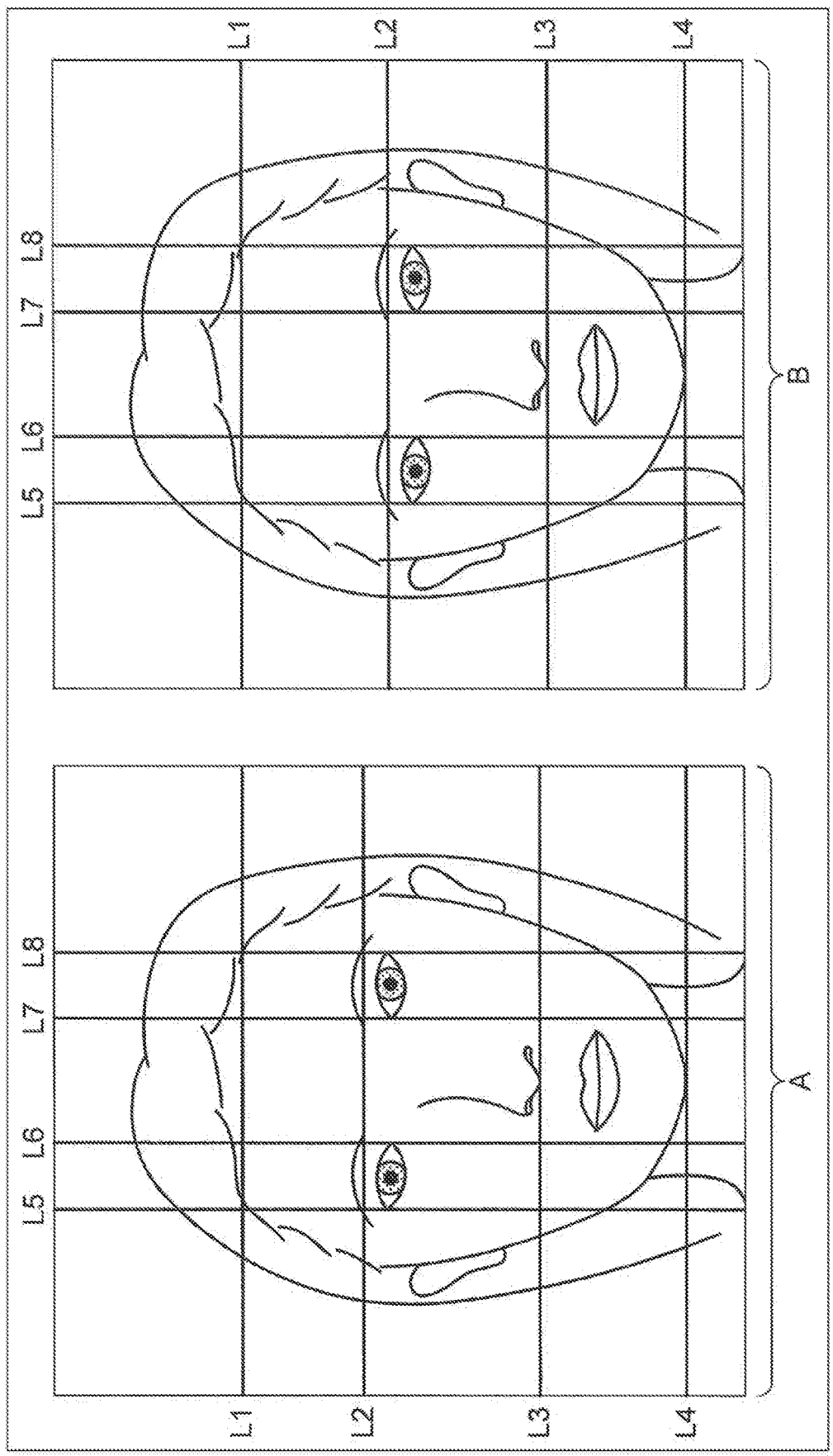

IMAGE PROCESSING DEVICE, IMAGE PROCESSING METHOD, AND NON-TRANSITORY COMPUTER-READABLE RECORDING MEDIUM STORING IMAGE PROCESSING PROGRAM

BACKGROUND

1. Technical Field

The present disclosure relates to an image processing device, an image processing method, and a non-transitory computer-readable recording medium storing an image processing program, that generate simulation images for makeup.

2. Description of the Related Art

In beautician schools, in classes for facial makeup (hereinafter, simply "makeup"), instructors commonly explain makeup methods using photographs and illustrations (showing specific examples of makeup) in paper-medium textbooks. Optimal makeup methods vary in accordance with facial features, so textbooks preferably include a greater number of specific examples of makeup. However, there is a limit to how far specific examples of makeup can be increased in textbooks, considering ease of carrying the textbooks. Accordingly, students cannot obtain a deeper understanding of specific examples of makeup suitable for various facial features. It is also troublesome and time-consuming for instructors to explain specific examples of makeup suitable for various facial features. Moreover, it is difficult for students to picture how makeup described in a textbook would look on a face that is different from the face in the textbook.

Accordingly, it is conceivable to use technology described in, for example, Japanese Unexamined Patent Application Publication No. 2016-81075, in order to describe a greater number of specific examples of makeup in accordance with various facial features. The technology in Japanese Unexamined Patent Application Publication No. 2016-81075 is a technology that changes features extracted from a facial image and changes the impression of the appearance of the facial image.

SUMMARY

However, even if the technology in Japanese Unexamined Patent Application Publication No. 2016-81075 is used, the instructor still has to explain in detail makeup methods suitable for the facial image after changing, verbally or the like. Accordingly, the problem of explanation being troublesome and time-consuming for the instructor is not resolved. Also, this results in the instructor explaining makeup methods verbally or the like, an accordingly is not sufficient regarding the point of the students obtaining a deeper understanding, either.

One non-limiting and exemplary embodiment provides an image processing device, an image processing method, and a non-transitory computer-readable recording medium storing an image processing program, whereby trouble and time for the instructor to explain makeup methods can be reduced, and students can obtain a deeper understanding of makeup methods.

In one general aspect, the techniques disclosed here feature an image processing device including: an image input unit that inputs a facial image from a predetermined device; an image analyzing unit that calculates one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image; and an image generating unit that decides a superimposing region of a makeup parts image based on one of the facial shape, the proportion lines, and the blocking lines, and generates a simulation image where the makeup parts image has been superimposed on the superimposing region.

According to the present disclosure, trouble and time for the instructor to explain makeup methods can be reduced, and students can obtain a deeper understanding of makeup methods.

It should be noted that general or specific embodiments may be implemented as a system, a device, a method, an integrated circuit, a computer program, a storage medium, or any selective combination of system, device, method, integrated circuit, computer program, and storage medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a flowchart illustrating a first operation example according to the present disclosure;

FIG. 4 is a diagram illustrating an example of proportion lines according to the present disclosure;

FIG. 9 is a diagram illustrating a display example of simulation images, before averaging and after averaging, according to the present disclosure;

DETAILED DESCRIPTION

Figure 1:
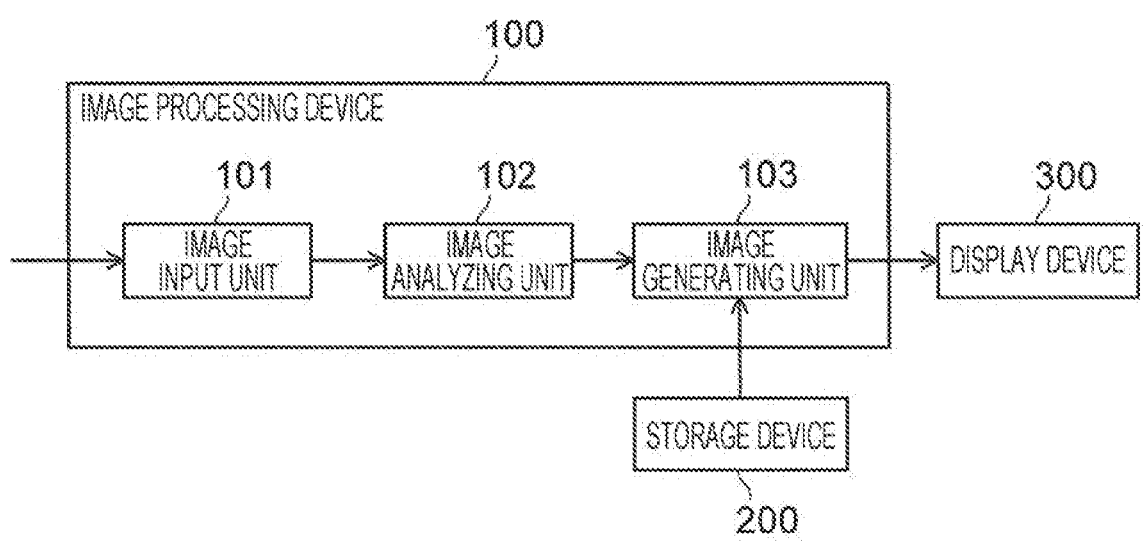
FIG. 1 is a block diagram illustrating an example of a configuration of an image processing device according to the present disclosure.

An embodiment of the present disclosure will be described in detail below with reference to the drawings.
Configuration of Image Processing Device First, the configuration of an image processing device 100 will be described with reference to FIG. 1. FIG. 1 is a block diagram illustrating an example of the configuration of the image processing device 100.

The image processing device 100 may be a stationary device, or may be a portable device that can be easily carried about. The image processing device 100, a storage device 200, and a display device 300, may be provided in, for example, a smartphone, a tablet terminal, a personal computer, or the like.

In the present embodiment, description will be made regarding an example of a case where the user of the image processing device 100 is an instructor teaching makeup methods in a beautician school or the like, or a student learning makeup methods in a beautician school or the like, for example. The image processing device 100 has an image input unit 101, an image analyzing unit 102, and an image generating unit 103, as illustrated in FIG. 1.

The image processing device 100 includes, for example, a central processing unit (CPU), storage media such as read only memory (ROM) or the like storing control programs, work memory such as random access memory (RAM) or the like, and a communication circuit, although omitted from illustration. The functions of the image input unit 101, image analyzing unit 102, and image generating unit 103 are realized by the CPU executing control programs, in this case.

The image input unit 101 inputs an image of a human face (hereinafter referred to as facial image) from a predetermined device (omitted from illustration), and outputs the facial image to the image analyzing unit 102. The predetermined device may be a camera, or may be the storage device 200, for example. The facial image may be a moving image or may be a still image. Note that the face in the facial image preferably is a face wearing no makeup.

The image analyzing unit 102 receives the facial image from the image input unit 101, and extracts facial feature points from the facial image. The image analyzing unit 102 also extracts facial parts (e.g., eyes, eyelids, cheeks, nose, lips, forehead, chin, and so forth), based on the facial feature points.

Figure 2:
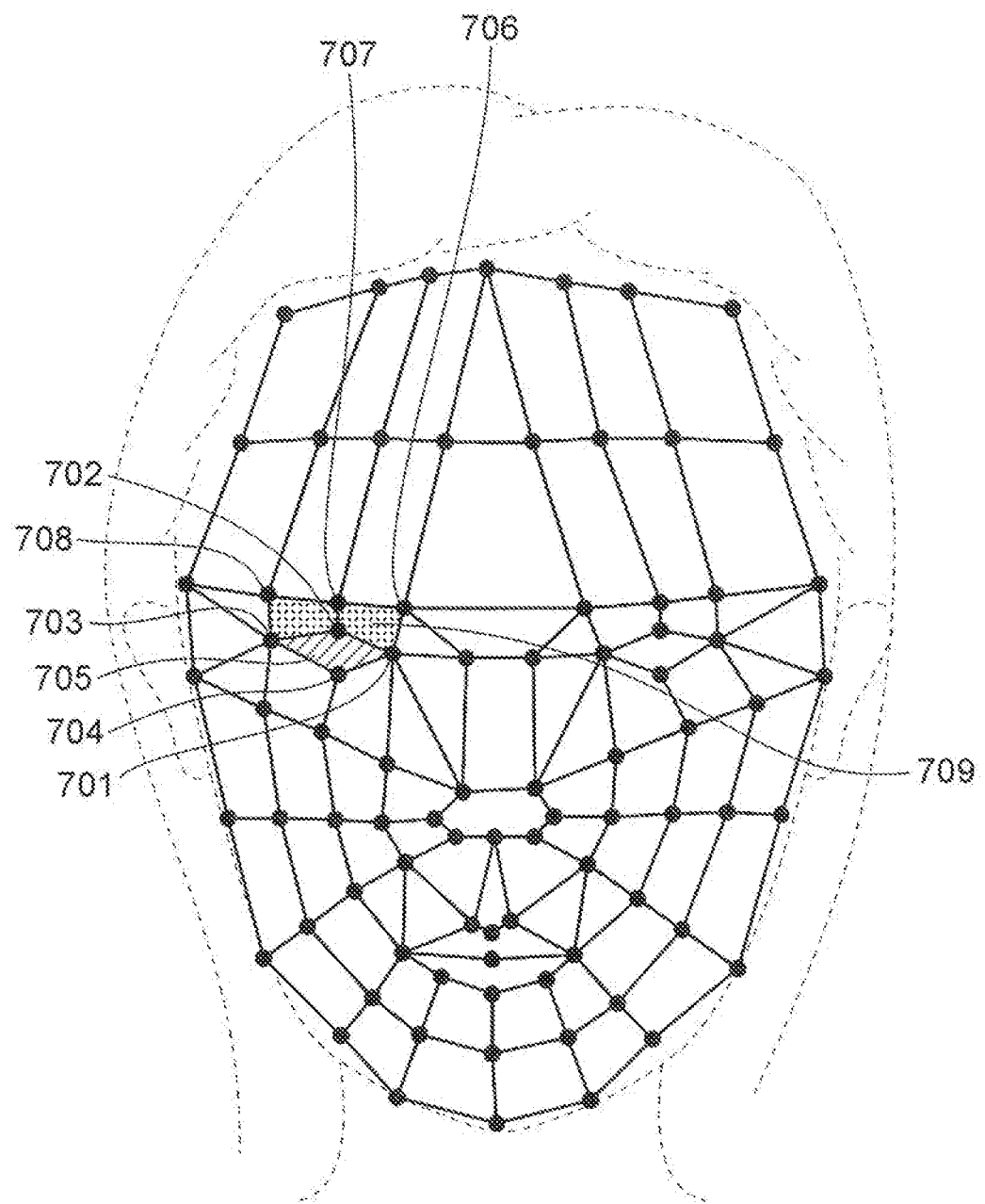
FIG. 2 is a diagram illustrating an example of facial feature points and facial parts according to the present disclosure.

Now, an example of facial feature points and facial parts will be described with reference to FIG. 2. As illustrated in FIG. 2 for example, multiple facial feature points (round dots in FIG. 2) are extracted from a facial image. For example, facial feature points 701 through 704 make up the right eye. Accordingly, the image analyzing unit 102 extracts a region 705 surrounded by the facial feature points 701 through 704 as being the right eye (example of facial part). Also, for example, facial feature points 701 through 703 and 706 through 708 make up the right eyelid. Accordingly, the image analyzing unit 102 extracts a region 709 surrounded by the facial feature points 701 through 703 and 706 through 708 as being the right eyelid (example of facial part).

Note that coordinates of the facial feature points are coordinates in a facial coordinate system set with multiple facial feature points as a reference, for example. The coordinates may be either two-dimensional coordinates or three-dimensional coordinates. This so far has been a description of an example of facial feature points and facial parts.

Returning to FIG. 1, the image analyzing unit 102 calculates, based on the facial feature points, either proportion lines that are lines drawn on the face to analyze the facial shape (shape of the outline of the frontal face), the balance of the face (balance of the overall face or balance of facial parts), or blocking lines that divide the face into multiple regions following the structure of the face (blocking), according to lightness and darkness of shadows due to light striking the face. Specific examples of facial shapes, proportion lines, and blocking lines will be described later in operation examples.

The image analyzing unit 102 then outputs the facial image, and analysis results information indicating analysis results of the facial image, to the image generating unit 103. Examples of analysis results information include information indicating the type of each facial part that that has been extracted, and information indicating coordinates of facial feature points enabling identification of each facial part that has been extracted. Examples of analysis results information also include information indicating coordinates of facial feature points enabling identification of facial shape, proportion lines, or blocking lines.

The image generating unit 103 receives the facial image and analysis results information from the image analyzing unit 102, and generates a simulation image where a makeup parts image is superimposed on the facial image, based on the analysis results information. The makeup parts image is an image indicating makeup regions and contrast, in order to overlay the facial image with makeup items (e.g., eye shadow, cheek color, concealer, lipstick, highlight, lowlight, etc.) of predetermined colors for performing makeup simulation. The makeup parts image is stored in the storage device 200, and read out from the storage device 200 by the image generating unit 103. Note that an arrangement may be made where the storage device 200 stores multiple types of makeup parts images with different colors and shapes for each makeup item, with the image generating unit 103 reading out makeup parts images specified by the user from these.

The image generating unit 103 then outputs the simulation image to the display device 300. The display device 300 displays the simulation image. Note that the facial image in the displayed simulation image may be a facial image such as that in a normal mirror, or may be a facial image in a flip mirror (horizontally inverting mirror). Examples of generating processing of simulation images will be described later in operation examples. The configuration of the image processing device 100 has been described so far.
Operations of Image Processing Device Next, operations of the image processing device 100 will be described. First through third operation examples will each be described below.

First Operation Example

First, a first operation example of the image processing device 100 will be described with reference to FIG. 3. FIG. 3 is a flowchart illustrating the first operation example of the image processing device 100.

First, the image input unit 101 inputs a facial image from a predetermined device (e.g., camera) (step S101). The image input unit 101 then outputs the facial image to the image analyzing unit 102.

Next, the image analyzing unit 102 extracts facial feature points from the facial image received from the image input unit 101 (step S102). The image analyzing unit 102 also extracts facial parts based on the facial feature points.

The image analyzing unit 102 calculates proportion lines next, based on the facial feature points (step S103).

An example of proportion lines will be described here with reference to FIG. 4. For example, the image analyzing unit 102 calculates proportion lines L1 through L4, as illustrated in FIG. 4. The proportion lines L1 through L4 are straight lines horizontal to the lateral width of the face, and are lines that divide the facial image in the vertical direction. The proportion lines L1 through L4 are proportion lines used to analyze the balance of the overall face.

The proportion line L1 is a straight line passing through facial feature points at the hairline on the forehead. The proportion line L2 is a straight line passing through facial feature points at the inner ends of the eyebrows. The proportion line L3 is a straight line passing through facial feature points at the nose tip. The proportion line L4 is a straight line passing through facial feature points at the tip of the chin.

The image analyzing unit 102 also calculates the width (distance) between proportion lines. For example, the image analyzing unit 102 calculates a width w1 between the proportion line L1 and the proportion line L2, a width w2 between the proportion line L2 and the proportion line L3, and a width w3 between the proportion line L3 and the proportion line L4, as illustrated in FIG. 4. An example of proportion lines has been described so far.

Returning to FIG. 3, next, the image analyzing unit 102 outputs the facial image and analysis results information to the image generating unit 103. This analysis results information includes, for example, information such as the types of the facial parts, coordinates of facial feature points enabling identification of the facial parts, coordinates of facial feature points enabling identification of the proportion lines L1 through L4, the widths w1 through w3 between the proportion lines, and so forth.

Next, the image generating unit 103 generates an image indicating the proportion lines based on the analysis results information (hereinafter referred to as proportion line image), and generates a simulation image where the proportion line image has been superimposed on the facial image (step S104). The image generating unit 103 then outputs the simulation image to the display device 300 (step S104). For example, the proportion line image is an image of each of the proportion lines L1 through L4 illustrated in FIG. 4.

The display device 300 displays the simulation image received from the image generating unit 103. Accordingly, the user can view the proportion line image on the facial image.

Next, the image generating unit 103 decides superimposing regions of makeup parts images (cheek color images here as an example) on the facial image, based on the analysis results information (Step 3105).

An example of superimposing region deciding processing (step S105) will be described here. For example, the image generating unit 103 determines which of the width w1 and width w3 illustrated in FIG. 4 is longer.

Figure 5A:
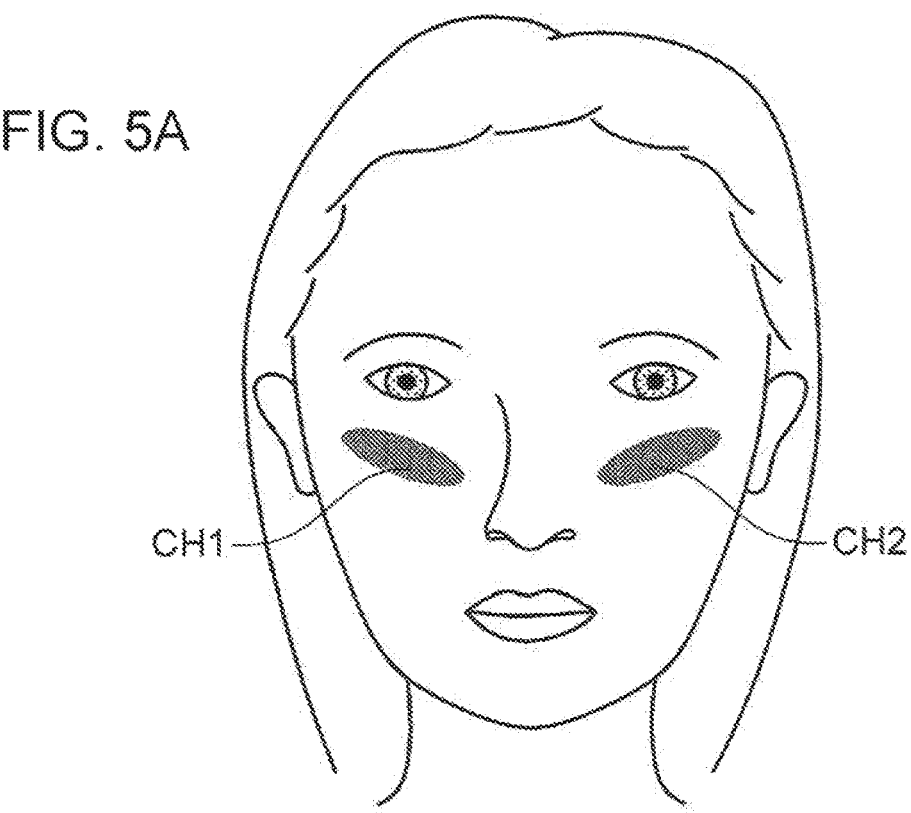
FIG. 5A is a diagram illustrating an example of superimposed regions of cheek color images according to the present disclosure.
Figure 5B:
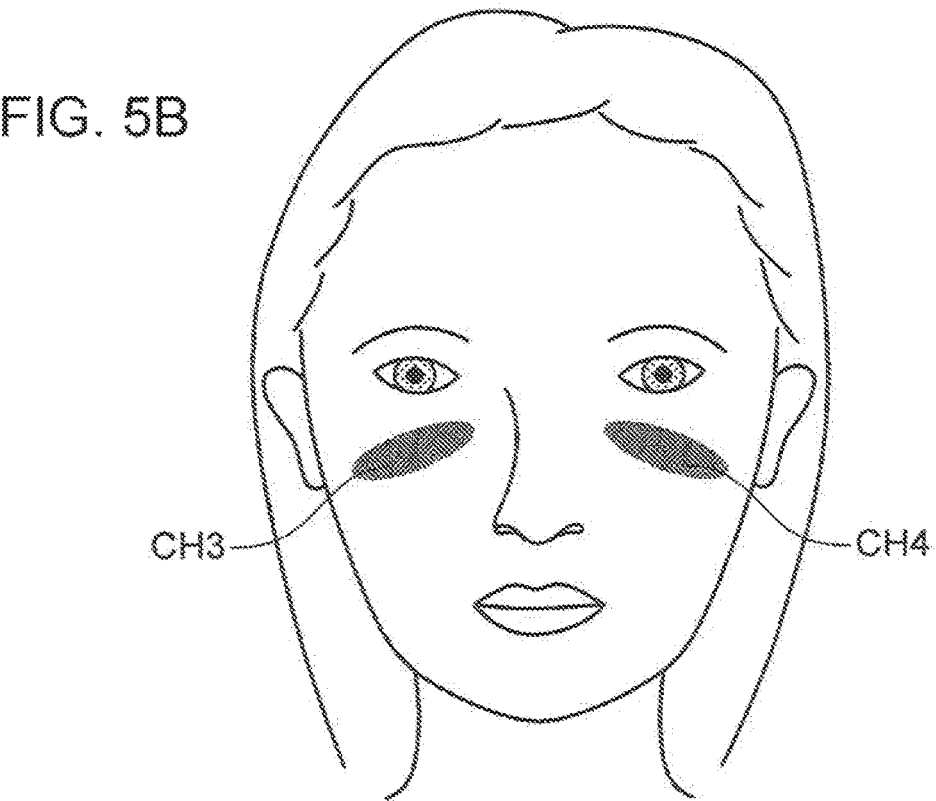
FIG. 5B is a diagram illustrating an example of superimposed regions on cheek color images according to the present disclosure.

In a case where width w1 is longer, cheek color image superimposing regions CH1 and CH2 on the facial image are decided so that the cheek color images are located upwards (with one end of the cheek color images near the outer ends of the eyes and the other end far from the inner ends of the eyes), as illustrated in FIG. 5A. On the other hand, in a case where width w3 is longer, cheek color image superimposing regions CH3 and CH4 on the facial image are decided so that the cheek color images are located downwards (with one end of the cheek color images near the inner ends of the eyes and the other end far from the outer ends of the eyes), as illustrated in FIG. 5B. An example of superimposing region deciding processing has been described so far.

Returning to FIG. 3, next, the image generating unit 103 reads out the cheek color images (e.g., images indicating pink ellipses of cheek color) from the storage device 200. Next, the image generating unit 103 adjusts the sizes and shapes of the cheek color images in accordance with the superimposing regions, and generates a simulation image where the cheek images have been superimposed on the superimposing regions (step S106). The image generating unit 103 then outputs the simulation image to the display device 300 (step 3106).

The display device 300 displays the simulation image received from the image generating unit 103. Accordingly, the user can visually recognize the cheek images on the facial image. Note that the display device 300 may display the simulation image generated in step S106, instead of the simulation image generated in step S104. In this case, the proportion line image is erased from the facial image, and only the cheek color image is displayed superimposed on the facial image. Alternatively, the display device 300 may display the cheek color image superimposed on the simulation image generated in step S104. In this case, both the proportion line image and the cheek color image are displayed superimposed on the facial image.

The first operation example of the image processing device 100 has been described so far. A modification of the first operation example will be described below.

First Modification of First Operation Example

The processing of step S104 in FIG. 3 may be omitted. That is to say, superimposed display of the proportion line image does not have to be performed.

Second Modification of First Operation Example

The processing of step S104 in FIG. 3 may be performed concurrently with the processing of step S106. That is to say, a simulation image where the proportion line image and the makeup parts image (e.g., cheek color image) are both superimposed on the facial image may be generated and output to the display device 300.

Third Modification of First Operation Example

Although description has been made above by way of an example where the makeup parts image is a cheek color image, the makeup parts image may be a makeup parts image other than cheek color, such as the above-described eye shadow, or the like, for example.

Fourth Modification of First Operation Example

The proportion lines that are calculated are not restricted to the proportion lines L1 through L4 illustrated in FIG. 4. Another example of proportion lines will be described below.

Figure 6:
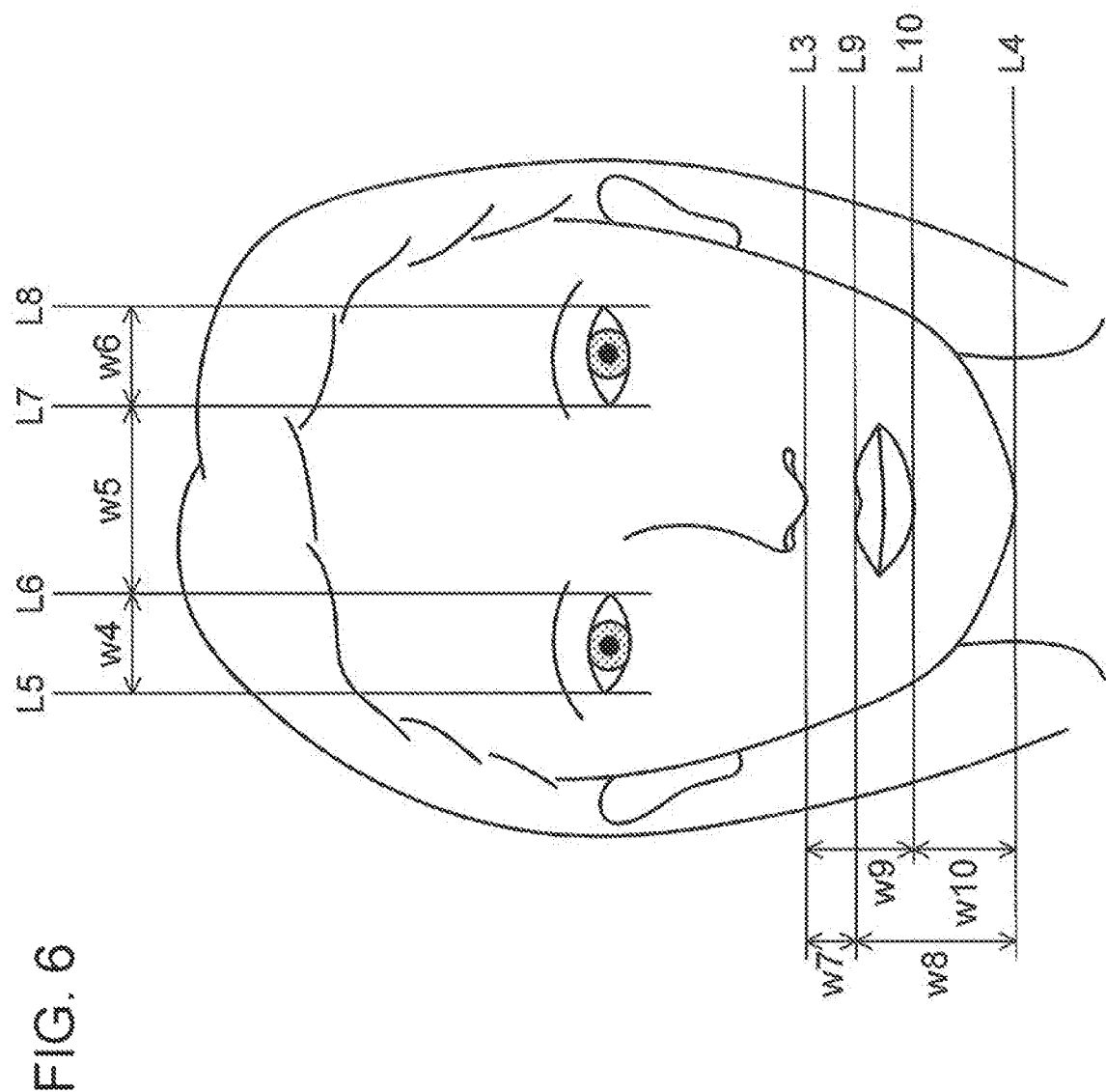
FIG. 6 is a diagram illustrating another example of proportion lines according to the present disclosure.

First, proportion lines L5 through L8 will be described with reference to FIG. 6. The proportion lines L5 through L8 illustrated in FIG. 6 are proportion lines used for analyzing the balance of the overall face. The proportion lines L5 through L8 are straight lines that are even with the vertical width of the face, and are lines that divide the facial image in the lateral direction.

The proportion line L5 is a straight line passing through facial feature points at the outer end of the right eye. The proportion line L6 is a straight line passing through facial feature points at the inner end of the right eye. The proportion line L7 is a straight line passing through facial feature points at the inner end of the left eye. The proportion line L8 is a straight line passing through facial feature points at the outer end of the left eye. The image analyzing unit 102 also calculates a width w4 between the proportion line L5 and the proportion line L6, a width w5 between the proportion line L6 and the proportion line L7, and a width w6 between the proportion line L7 and the proportion line L8.

Next, proportion lines L9 and L10 will be described with reference to FIG. 6. The proportion lines L9 and L10 illustrated in FIG. 6 are proportion lines used for analyzing the balance of the overall face. The proportion lines L9 and L10 are straight lines that are horizontal with the lateral width of the face, and are lines that divide the facial image in the vertical direction. The proportion line L9 is a straight line passing through facial feature points at the upper lip. The proportion line L10 is a straight line passing through facial feature points at the lower lip. The image analyzing unit 102 also calculates a width w7 between the proportion line L3 and the proportion line L9, a width w8 between the proportion line L9 and the proportion line L4, a width w9 between the proportion line L3 and the proportion line L10, and a width w10 between the proportion line L10 and the proportion line L4, for example.

Figure 7:
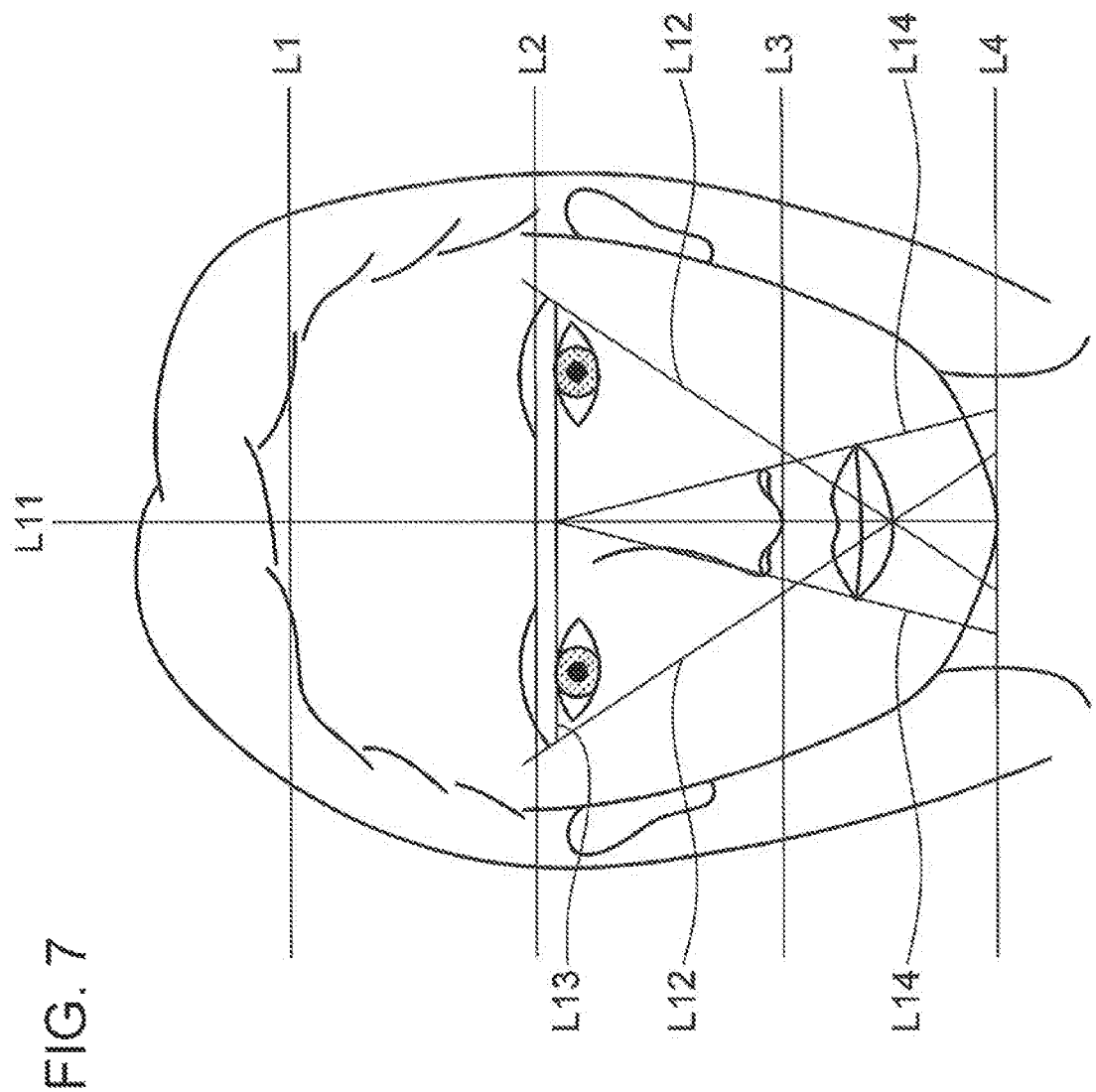
FIG. 7 is a diagram illustrating another example of proportion lines according to the present disclosure.

Next, proportion lines L11 through L14 will be described with reference to FIG. 7. Note that the proportion lines L1 through L4 illustrated in FIG. 7 have already been described with reference to FIG. 4, and according description thereof will be omitted here. The proportion lines L11 through L14 illustrated in FIG. 7 are proportion lines used for analyzing the balance of the overall face.

The proportion line L11 is a straight line passing through facial feature points at the ridge of the nose (e.g., root of the nose, dorsum of the nose, tip of the nose). The proportion lines L12 are straight lines passing through facial feature points at the outer ends of the eyebrows, facial feature points at the outer ends of the eyes, and facial feature points to the outer side of the wings of the nose. The proportion line L13 is a straight line passing through facial feature points at the upper end of the right pupil and facial feature points at the upper end of the left pupil. The proportion lines L14 are straight lines passing through an intersection point of the proportion line L11 and proportion line L13, and facial feature points at the outer side of the wings of the nose.

Figure 8A:
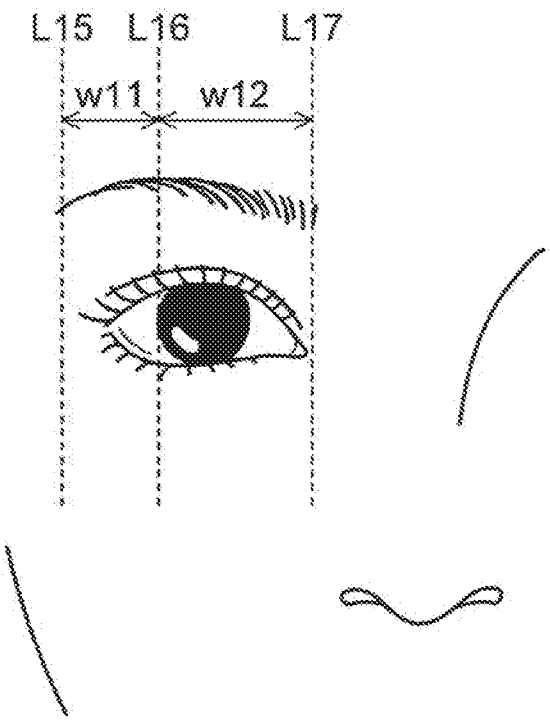
FIG. 8A is a diagram illustrating another example of proportion lines according to the present disclosure.

Next, proportion lines L15 through L29 will be described with reference to FIGS. 8A through 8C. The proportion lines L15 through L17 illustrated in FIG. 8A are proportion lines used for analyzing the balance of the eyebrow (example of a facial part). The proportion lines L15 through L17 are straight lines that are even with the vertical width of the face.

In FIG. 8A, the proportion line L15 is a straight line passing through facial feature points at the outer end of the right eyebrow. The proportion line L16 is a straight line passing through facial feature points at the peak of the arch of the right eyebrow. The proportion line L17 is a straight line passing through facial feature points at the inner end of the right eyebrow. The image analyzing unit 102 also calculates a width w11 between the proportion line L15 and the proportion line L16, and a width w12 between the proportion line L16 and the proportion line L17.

Figure 8B:
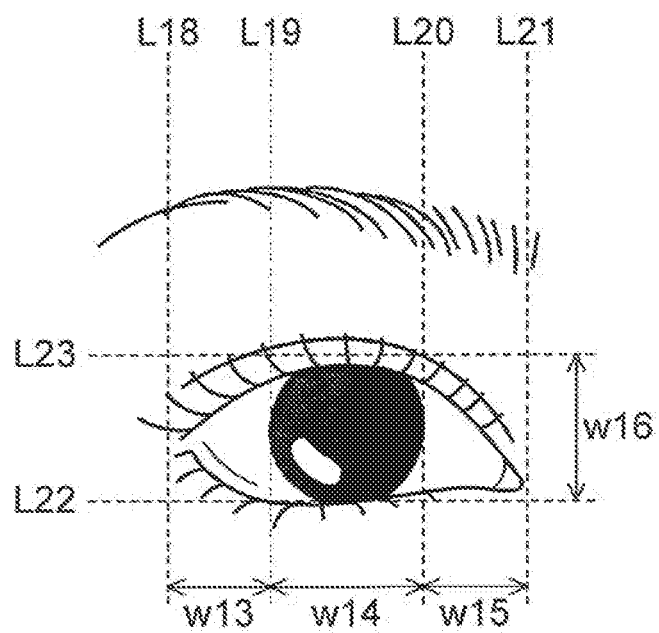
FIG. 8B is a diagram illustrating another example of proportion lines according to the present disclosure.

The proportion lines L18 through L23 illustrated in FIG. 8B are proportion lines used for analyzing the balance of the eye (example of a facial part). The proportion lines L18 through L21 are straight lines that are even with the vertical width of the face, and the proportion lines L22 and L23 are straight lines that are horizontal with the lateral width of the face. In FIG. 8B, the proportion line L18 is a straight line passing through facial feature points at the outer end of the right eye. That is to say, the proportion line L18 is the same as the proportion line L5 illustrated in FIG. 6. The proportion line L19 is a straight line passing through facial feature points at the right edge of the pupil of the right eye. The proportion line L20 is a straight line passing through facial feature points at the left edge of the pupil of the right eye. The proportion line L21 is a straight line passing through facial feature points at the inner end of the right eye. That is to say, the proportion line L21 is the same as the proportion line L6 illustrated in FIG. 6. The proportion line L22 is a straight line passing through facial feature points at the lower edge of the right pupil. The proportion line L23 is a straight line passing through facial feature points at the upper edge of the right pupil.

The image analyzing unit 102 also calculates a width w13 between the proportion line L18 and the proportion line L19, a width w14 between the proportion line L19 and the proportion line L20, a width w15 between the proportion line L20 and the proportion line L21, and a width w16 between the proportion line L22 and the proportion line L23.

Figure 8C:
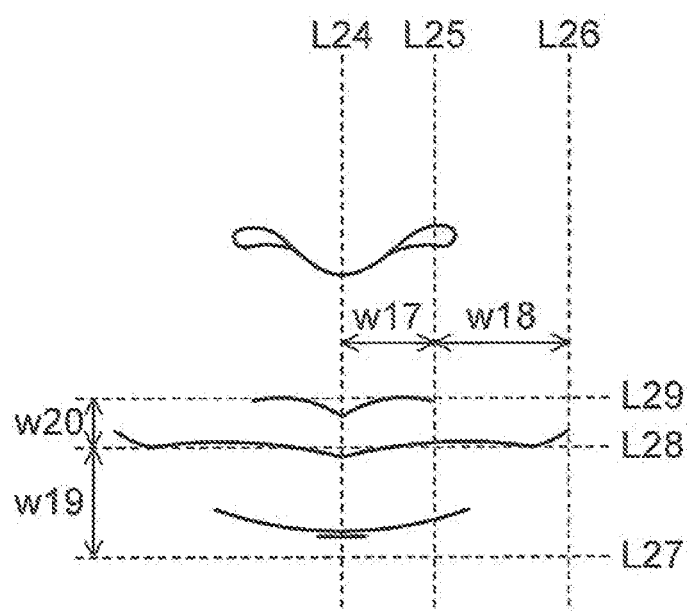
FIG. 8C is a diagram illustrating another example of proportion lines according to the present disclosure.

The proportion lines L24 through L29 illustrated in FIG. 8C are proportion lines used for analyzing the balance of the mouth (example of a facial part). The proportion lines L24 through L26 are straight lines that are even with the vertical width of the face, and the proportion lines L27 through L29 are straight lines that are horizontal with the lateral width of the face. In FIG. 8C, the proportion line L24 is a straight line passing through facial feature points at the tip of the nose and facial feature points at the center of the lips. The proportion line L25 is a straight line passing through facial feature points at the center of the left nostril. The proportion line L26 is a straight line passing through facial feature points at the left edge of the lips. The proportion line L27 is a straight line passing through the lower edge of the lower lip. The proportion line L28 is a straight line passing through facial feature points at the boundary between the upper lip and lower lip. The proportion line L29 is a straight line passing through the upper edge of the upper lip.

The image analyzing unit 102 also calculates a width w17 between the proportion line L24 and the proportion line L25, a width w18 between the proportion line L25 and the proportion line L26, a width w19 between the proportion line L27 and the proportion line L28, and a width w20 between the proportion line L28 and the proportion line L29.

Fifth Modification of First Operation Example

The positions of the above-described proportion lines L1 through L29 may be changed based on user instructions, for example. Specifically, an arrangement may be made where, in a case of having received an instruction to change the position of a predetermined proportion line, the image generating unit 103 generates a facial image where at least one of the shape and position of a facial part in the facial image has been changed based on the position of a proportion line after changing (hereinafter referred to as post-change facial image), and outputs the post-change facial image to the display device 300. Alternatively, the image generating unit 103 may generate a simulation image where a proportion line image is superimposed on the post-change facial image, and output to the display device 300.

Also, an arrangement may be made where, in a case of having received an instruction to equalize the facial balance in the facial image (hereinafter, also referred to simply as "equalization"), the image generating unit 103 changes the position of a predetermined proportion line so that the widths between the proportion lines have the same ratios.

For example, in a case of having received an instruction for equalization after having calculated the proportion lines L1 through L4 illustrated in FIG. 4 and the proportion lines L5 through L8 illustrated in FIG. 6, the image generating unit 103 changes the position of at least one of the proportion lines L1 through L4 so that the ratios of the widths w1 through w3 in FIG. 4 are 1:1:1, and changes the position of at least one of the proportion lines L5 through L8 so that the ratios of the widths w4 through w6 in FIG. 6 are 1:1:1.

Now, FIG. 9 illustrates a display example of a simulation image obtained as a result of the above-described equalization. A simulation image A illustrated in FIG. 9 is an example of a simulation image before equalization. On the other hand, a simulation image B illustrated in FIG. 9 is an example of a simulation image after equalization. The simulation images A and B are images where the proportion lines L1 through L8 have been superimposed on a facial image, as illustrated in FIG. 9.

In comparison with the simulation image A, the simulation image B has had the positions of the proportion lines L2 and L3 changed, and the positions of the eyebrows and eyes have been changed. Thus, displaying two simulation images side by side allows easy comparison by the user between a face where the facial balance has not been equalized and a face where the facial balance has been equalized.

Although equalization processing where the positions of proportion lines are changed so that the widths have the same ratio (e.g., 1:1:1) has been described in the above description, idealization processing may be performed, for example, where the positions of proportion lines are hanged so that the ratio of the widths is an ideal ratio that has been set beforehand. Examples of changing the position of proportion lines in a case of having received an instruction for idealization of facial balance in a facial image will each be described below.

For example, the position of at least one of proportion lines L3, L9, and L4 in FIG. 6 may be changed so that the ratio of the width w7 and width w8 is 1:3. Also, the position of at least one of proportion lines L3, L10, and L4 in FIG. 6 may be changed so that the ratio of the width w9 and width w10 is 1:1.

Also, for example, the position of at least one of proportion lines L15 through L17 in FIG. 8A may be changed so that the ratio of the width WI 1 and width w12 is 1:2. Also, for example, the position of at least one of proportion lines L18 through L23 in FIG. 8B may be changed so that the ratio of the widths w13 through W16 1:1:1:1. Also, for example, the position of at least one of proportion lines L24 through L26 in FIG. 8C may be changed so that the ratio of the width w17 and width w18 is 1:2. Also, for example, the position of at least one of proportion lines L27 through L29 in FIG. 8C may be changed so that the ratio of the width w19 and width w20 is 1.5:1.

Examples of changing the positions of proportion lines in a case of idealization having been instructed has thus been described. In these examples as well, a post-change facial image where at least one of the position and shape of a facial part has been change is generated based on the changed proportion lines, as described above.

Sixth Modification of First Operation Example

An example has been described above regarding a case of deciding superimposing regions for cheek color images based on comparison results of width w1 and width w3, but this is not restrictive. Other examples will be described below.

For example, the image analyzing unit 102 calculates the vertical width of the outline (e.g., may be proportion lines indicating the maximum vertical width) and lateral width of the outline (e.g., may be proportion lines indicating the maximum lateral width) based on facial feature points, when performing the calculation processing of proportion lines (step S103 in FIG. 3). the calculation results thereof are included in the analysis results information and output to the image generating unit 103.

The image generating unit 103 determines which of the calculated vertical width and lateral width is longer, in the superimposition region deciding processing (step S105 in FIG. 3). In a case where the vertical width is longer (in a case where the facial shape is an oblong face), the superimposing region of the cheek color images on the facial image is decided so that elliptical cheek color images are laid out sideways (so that the long axis of the ellipse is parallel to the lateral width of the face), for example. On the other hand, in a case where the lateral width is longer (in a case where the facial shape is a round face), the superimposing region of the cheek color images on the facial image is decided so that elliptical cheek color images are laid out obliquely from the cheeks toward the corners of the mouth, for example. Modification of the first operation example have thus been described.

Second Operation Example

Figure 10:
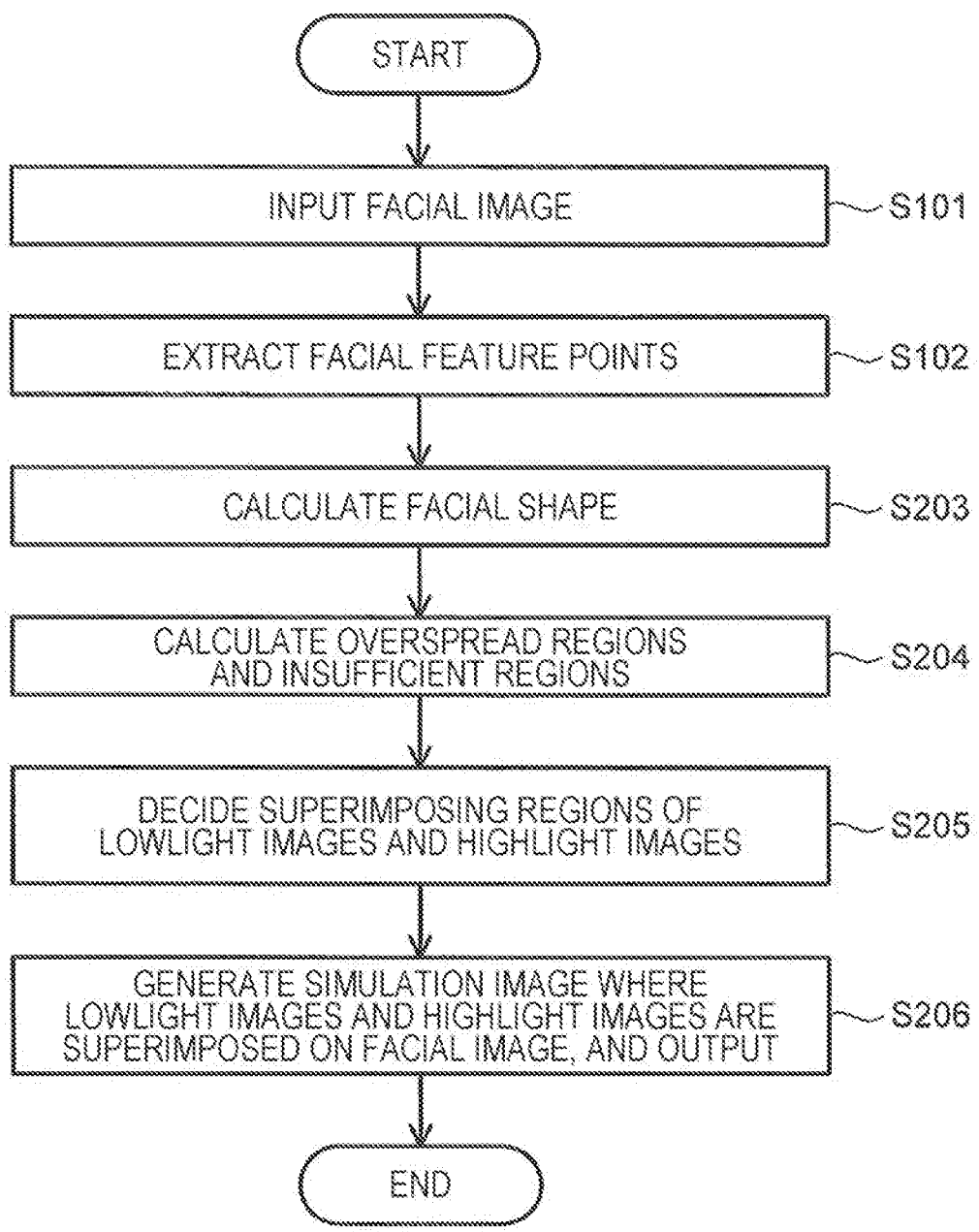
FIG. 10 is a flowchart illustrating a second operation example according to the present disclosure.

Next, a second operation example of the image processing device 100 will be described with reference to FIG. 10. FIG. 10 is a flowchart illustrating the second operation example of the image processing device 100. Steps S101 and S102 have already been described in the first operation example, so description here will be omitted.

Next, the image analyzing unit 102 calculates the facial shape based on the facial feature points (step S203). The facial shapes calculated here (hereinafter referred to as calculated facial shape) are, for example, triangular, diamond, round, oblong, rectangular, octagonal, and so forth.

Next, image analyzing unit 102 outputs the facial image and the analysis results information to the image generating unit 103. The analysis results information includes, for example, types of the facial parts, coordinates of facial feature points enabling identification of the facial parts, coordinates of facial feature points enabling identification of calculated facial shape, and so forth.

Next, the image generating unit 103 reads information of a standard facial shape out from the storage device 200. The standard facial shape is a facial shape decided beforehand, and is, for example, an oval shape that is an ideal face form.

Next, the image generating unit 103 matches the calculated facial shape and the standard facial shape by matching the size of the standard facial shape to the size of the calculated facial shape, and calculates overspread regions and insufficient regions (step S204).

Next, the image generating unit 103 decides the superimposing region of a makeup parts image (lowlight image and highlight image here, as an example) to be superimposed on the facial image, based on the overspread regions and insufficient regions (step S205).

Examples of region calculation processing (step S204) and superimposing region deciding processing (step S205) will be described here, with reference to FIGS. 11A through 12B. Region calculation processing and superimposing region deciding processing in a case where the calculated facial shape is triangular will be described with reference to FIGS. 11A and 11B.

Figure 11A:
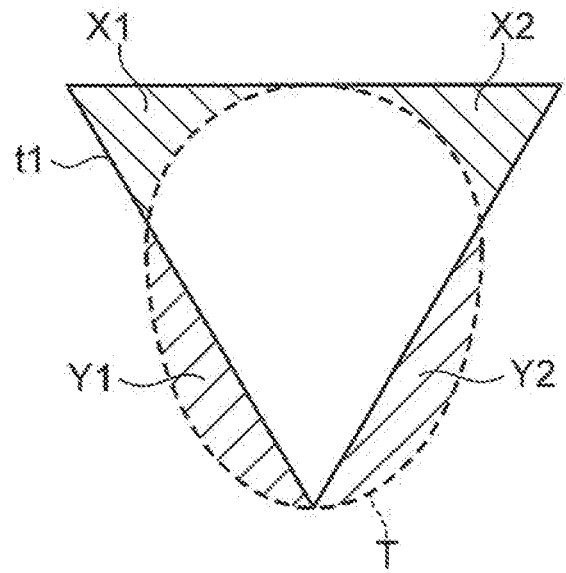
FIG. 11A is a diagram illustrating an example of matching facial shapes, according to the present disclosure.

First, the image generating unit 103 matches the triangular calculated facial shape t1 with the oval reference facial shape T, as illustrated in FIG. 11A. The image generating unit 103 then calculates overspread regions X1 and X2 where the calculated facial shape t1 spreads out from the reference facial shape T. The image generating unit 103 also calculates insufficient regions Y1 and Y2 where the calculated facial shape t1 does not fill out the reference facial shape T.

Figure 11B:
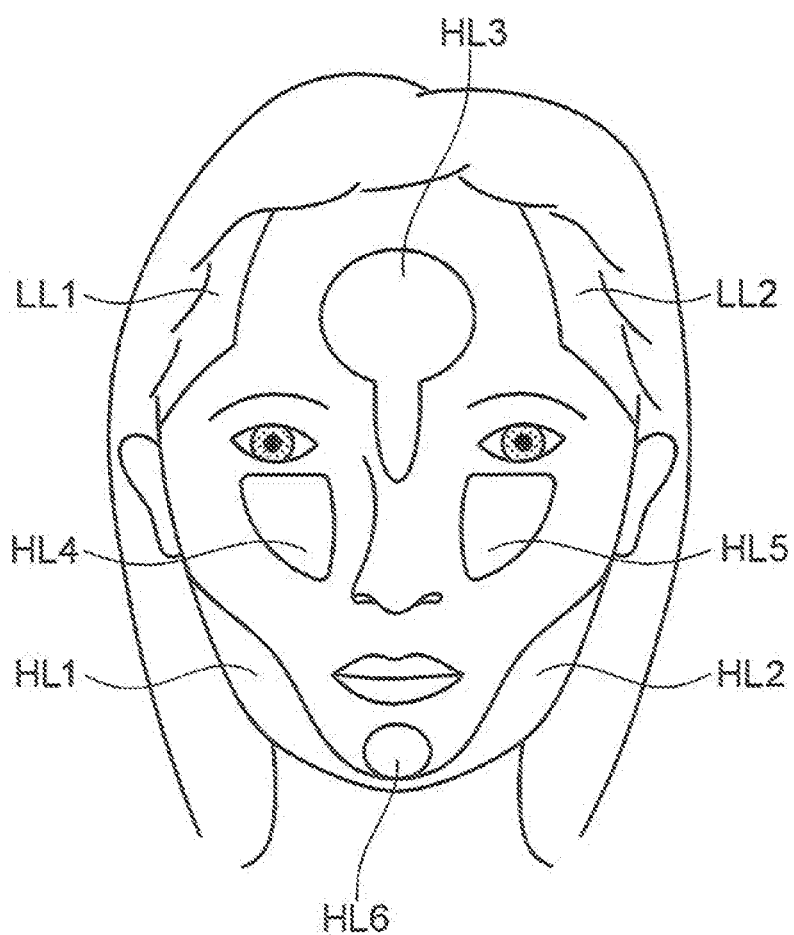
FIG. 11B is a diagram illustrating an example of superimposed regions of lowlight images and highlight images for facial shapes, according to the present disclosure.

Next, the image generating unit 103 decides regions LL1 and LL2 corresponding to the overspread regions X1 and X2 of the facial image to be lowlight image superimposing regions, as illustrated in FIG. 11B. The image generating unit 103 also decides regions HL1 and HL2 corresponding to the insufficient regions Y1 and Y2 of the facial image to be highlight image superimposing regions, as illustrated in FIG. 11B.

Also, as illustrated in FIG. 11B, the image generating unit 103 decides a region HL3 (region of forehead and nose ridge), region HL4 (region below the right eye), region HL5 (region below the left eye), and region HL6 (region of the chin), as highlight image superimposing regions. These regions HL3 through HL6 are decided beforehand as highlight image superimposing regions common to all face forms, but the sizes and shapes are changed as appropriate in accordance with features of the facial image (calculated facial shape).

Figure 12A:
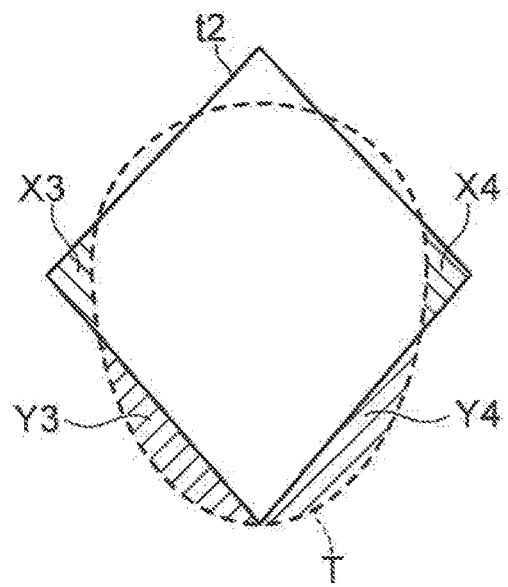
FIG. 12A is a diagram illustrating an example of matching facial shapes, according to the present disclosure.

Region calculation processing and superimposing region deciding processing in a case where the calculated facial shape is a diamond shape will be described with reference to FIGS. 12A and 12B. First, the image generating unit 103 matches the diamond-shaped calculated facial shape t2 with the oval reference facial shape T, as illustrated in FIG. 12A. The image generating unit 103 then calculates overspread regions X3 and X4 where the calculated facial shape t2 spreads out from the reference facial shape T. The image generating unit 103 also calculates insufficient regions Y3 and Y4 where the calculated facial shape t2 does not fill out the reference facial shape T.

Figure 12B:
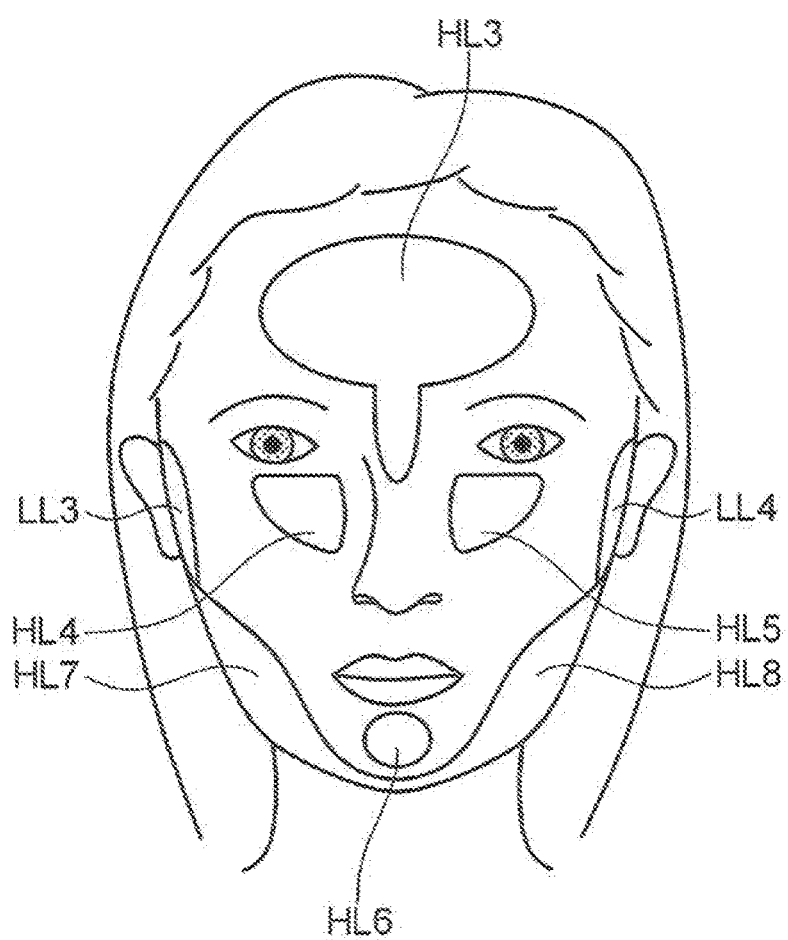
FIG. 12B is a diagram illustrating an example of superimposed regions of lowlight images and highlight images for facial shapes, according to the present disclosure.

Next, the image generating unit 103 decides regions LL3 and LL4 corresponding to the overspread regions X3 and X4 of the facial image to be lowlight image superimposing regions, as illustrated in FIG. 12B. The image generating unit 103 also decides regions HL7 and HL8 corresponding to the insufficient regions Y3 and Y4 of the facial image to be highlight image superimposing regions, as illustrated in FIG. 12B. The image generating unit 103 also decides regions HL3 through HL6 to be highlight image superimposing regions, as illustrated in FIG. 12B. Examples of region calculation processing and superimposing region deciding processing have thus been described.

Returning to FIG. 10, next, the image generating unit 103 reads out lowlight images and highlight images from the storage device 200. The image generating unit 103 then adjusts the sizes and shapes of the lowlight images and highlight images in accordance with the superimposing regions, and generates a simulation image where the lowlight images and highlight images have been superimposed on the superimposing regions (step S206). The image generating unit 103 outputs the simulation image to the display device 300, next (Step S206).

The display device 300 displays the simulation image received from the image generating unit 103. Accordingly, the user can visually recognize the lowlight images and highlight images on the facial image. The second operation example of the image processing device 100 has thus been described. Modifications of the second operation example will be described next.

First Modification of Second Operation Example

Although description has been made above giving an example of a case where the makeup parts images are lowlight images and highlight images, The makeup parts images may be images of makeup items other than lowlights and highlights.

Second Modification of Second Operation Example

Although description has been made above giving an example of a case where the calculated facial shape is triangular or diamond-shaped, the calculated facial shape may be round, oblong, rectangular, or octagonal.

Third Modification of Second Operation Example

Although description has been made above giving an example of a case where both overspread regions and insufficient regions are calculated, there may be cases where only one of overspread regions and insufficient regions is calculated, depending on the matching results.

Also, even in a case where both overspread regions and insufficient regions are calculated, there is no need to decide all calculated regions to be superimposing regions. For example, in cases where superimposing highlight images in regions corresponding to insufficient regions in the facial image results in an unnatural appearance, such insufficient regions are not decided to be superimposing regions. Modifications of the second operation example have thus been described.

Third Operation Example

Figure 13:
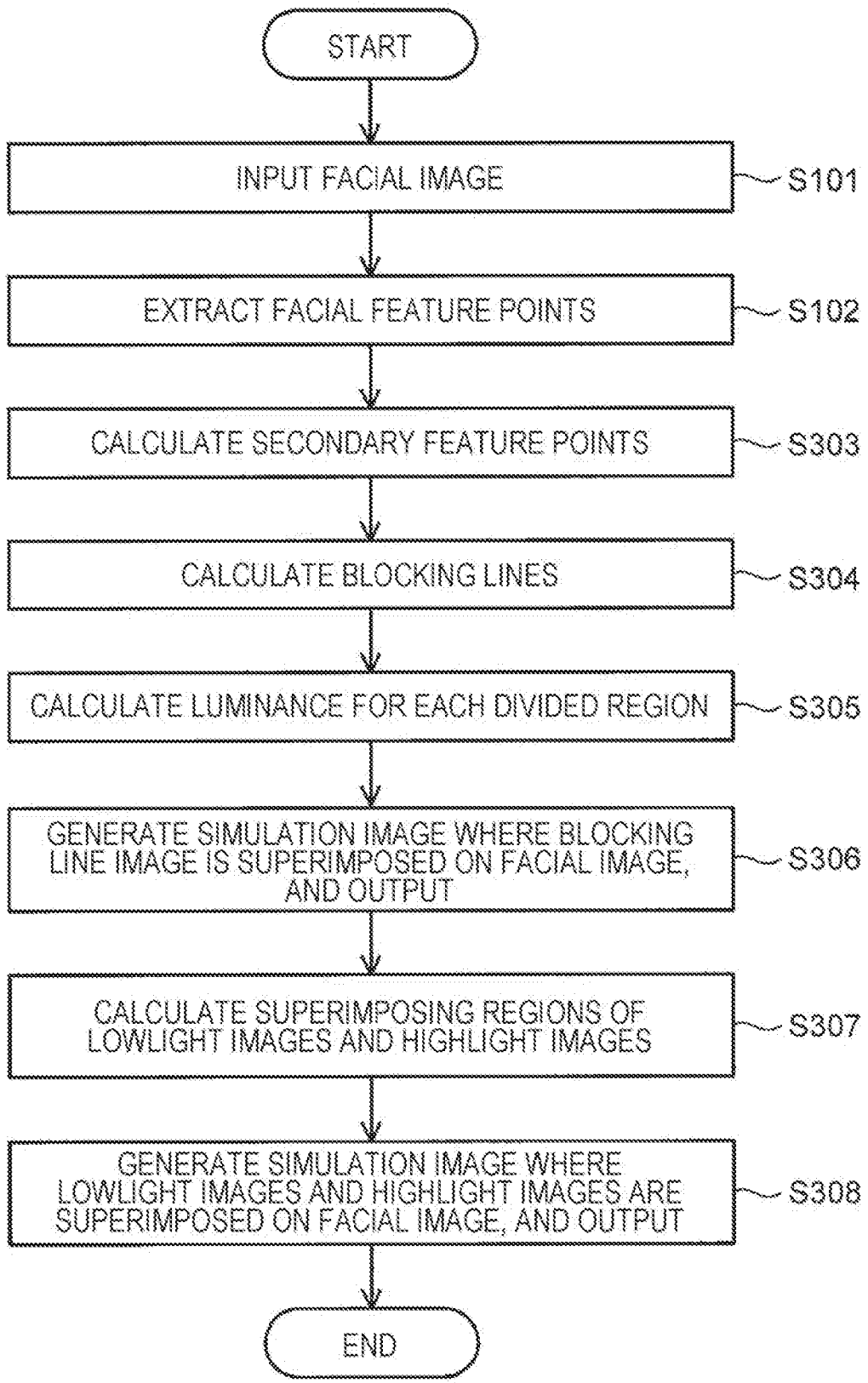
FIG. 13 is a flowchart illustrating a third operation example according to the present disclosure.

Next, a third operation example of the image processing device 100 will be described with reference to FIG. 13. FIG. 13 is a flowchart illustrating the third operation example of the image processing device 100. Steps S101 and S102 have already been described in the first operation example, so description here will be omitted.

Next, the image analyzing unit 102 calculates secondary feature points based on the facial feature points (step S303). Secondary feature points are, for example, points dividing line segments between facial feature points (hereinafter referred to simply as "line segment"), points on extensions of line segments, intersection points of two line segments, and so forth.

Next, the image analyzing unit 102 calculates blocking lines based on the facial feature points and secondary feature points (step S304).

Next, the image analyzing unit 102 calculates the luminances of divided regions sectioned by the blocking lines (step S305).

Figure 14:
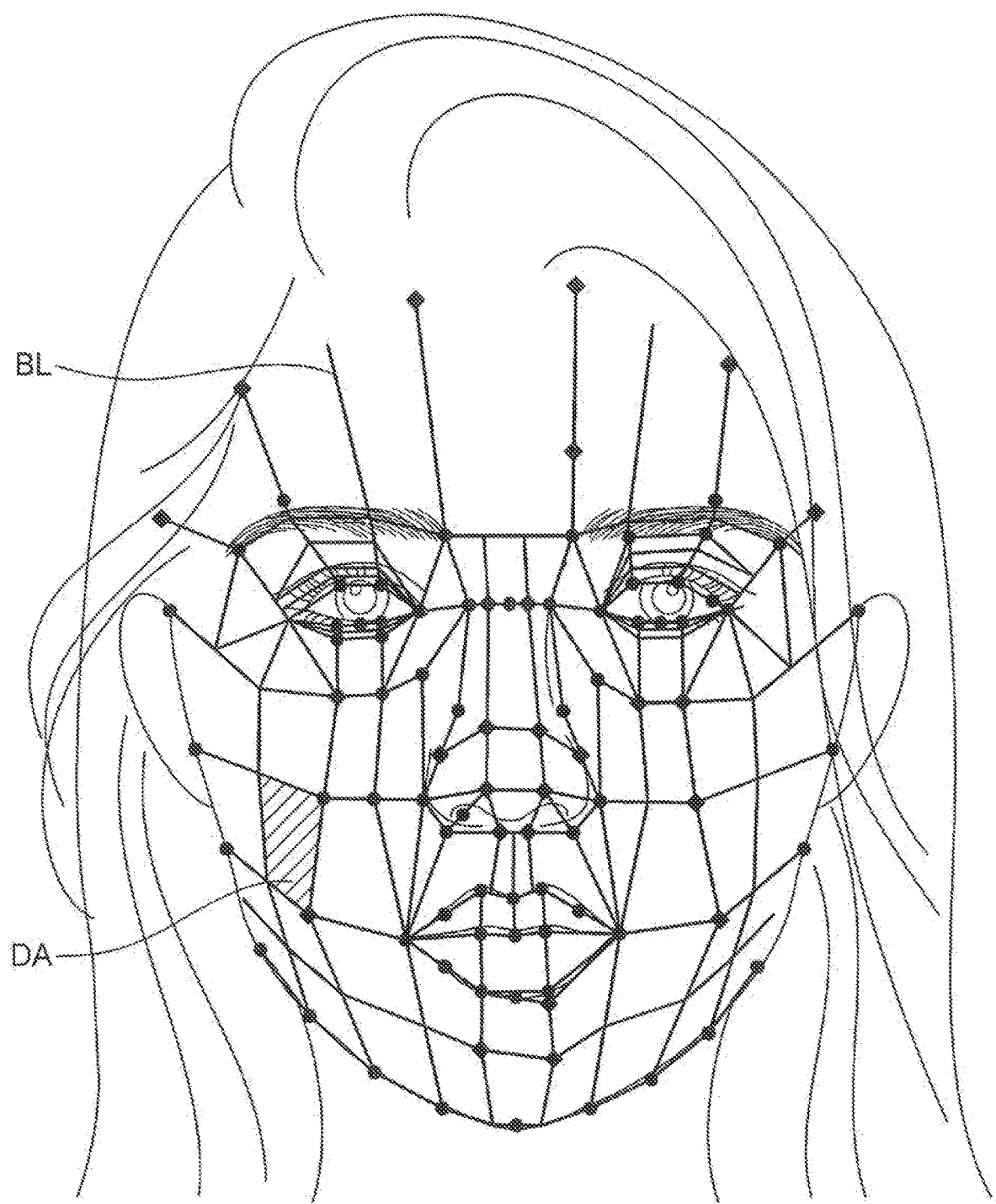
FIG. 14 is a diagram illustrating an example of blocking lines according to the present disclosure.

An example of blocking lines and divided regions will be described here with reference to FIG. 14. For example, the image analyzing unit 102 calculates blocking lines BL, as illustrated in FIG. 14. The round dots in FIG. 14 represent facial feature points, and the squares represent secondary feature points. Also, a divided region DA indicates one of multiple divided regions sectioned by the blocking lines BL in FIG. 14. An example of blocking lines and divided regions has thus been described.

Returning to FIG. 13, next, the image analyzing unit 102 outputs the facial image and analysis results information to the image generating unit 103. The analysis results information includes, for example, types of the facial parts, coordinates of facial feature points enabling identification of the facial parts, coordinates of facial feature points and secondary feature points enabling identification of blocking lines BL, coordinates of facial feature points and secondary feature points enabling identification of divided regions, luminance of each divided region, and so forth.

Next, the image generating unit 103 generates an image indicating blocking lines (hereinafter referred to as blocking line image) based on the analysis results information, and generates a simulation image where the blocking line image has been superimposed on the facial image (step S306). The image generating unit 103 outputs the simulation image to the display device 300 (step S306). For example, the blocking line image is an image showing the blocking lines BL illustrated in FIG. 14. Note that facial feature points and secondary feature points may be included in this blocking line image.

The display device 300 displays the simulation image received from the image generating unit 103. Accordingly, the user can visually recognize the blocking line image on the facial image.

Next, the image generating unit 103 decides superimposing regions of the makeup parts image on the facial image (lowlight images and highlight images here as an example) based on the analysis results information (step S307).

An example of superimposing region deciding processing (step S307) will be described here. First, the image generating unit 103 determines whether or not the luminance of each divided region is equal to or greater than a first threshold value that has been set beforehand. The image generating unit 103 then decides divided regions where the luminance is greater than the first threshold value to be highlight image superimposing regions.

On the other hand, if the luminance is smaller than the first threshold value, the image generating unit 103 determines whether or not the luminance smaller than a second threshold value. The second threshold value is a smaller value than the first threshold value. The image generating unit 103 then decides divided regions where the luminance is smaller than the second threshold value to be lowlight image superimposing regions.

On the other hand, the image generating unit 103 sets divided regions that are smaller than the first threshold value but equal to or larger than the second threshold value to be non-superimposing regions. Non-superimposing regions are regions where neither highlight images nor lowlight images are superimposed. An example of superimposing region deciding processing has thus been described.

Returning to FIG. 13, next, the image generating unit 103 reads out lowlight images and highlight images from the storage device 200. The image generating unit 103 then adjusts the sizes and shapes of the lowlight images and highlight images to match the superimposing regions, and generates a simulation image where the lowlight images and highlight images have been superimposed on the superimposing regions (step S308). The image generating unit 103 then outputs the simulation image to the display device 300 (step S308).

The display device 300 displays the simulation image received from the image generating unit 103. Accordingly, the user can visually recognize lowlight images and highlight images on the facial image. The third operation example of the image processing device 100 has thus been described. Modifications of the third operation example will be described below.

First Modification of Third Operation Example

Although description has been made above regarding an example of a case where the makeup parts image is lowlight images and highlight images, the makeup parts image may be makeup items other than lowlights and highlights.

Second Modification of Third Operation Example

Although description has been made above regarding an example of a case where blocking lines are calculated based on facial feature points and secondary feature points, blocking lines may be calculated based on facial feature points alone. Modifications of the third operation example, and operations of the image processing device 100, have thus been described.

Advantages of Present Embodiment

As described above, the image processing device 100 according to the present embodiment is a device that generates a simulation image for makeup. The image processing device 100 includes the image input unit 101 that inputs a facial image from a predetermined device, the image analyzing unit 102 that calculates one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image, and the image generating unit 103 that generates a simulation image where a makeup parts image has been superimposed in the facial image based on one of the facial shape, proportion lines and blocking lines, and outputs the simulation image to the display device 300. Thus, according to the present embodiment, trouble and time for the instructor to explain makeup methods can be reduced, and students can obtain a deeper understanding of makeup methods.

MODIFICATIONS OF PRESENT DISCLOSURE

An embodiment of the present disclosure has been described above, but the present disclosure is not restricted to the above description, and various modification can be made. Modifications will be described below.

First Modification

In a case where a user selects a makeup parts image included in a simulation image during display of the simulation image, the image processing device 100 may output a method and so forth of applying that makeup item, to the display device 300 as a makeup guide image superimposed on the facial image, or guide information in the form of text, photographs, illustrations, audio, or the like. Guide information is stored in the storage device 200 in correlation with each makeup parts image. Note that the guide information may be still images or moving images. The display device 300 may have an audio output (speaker) function (which is true for the following modifications as well).

For example, when generating a simulation image, the image generating unit 103 reads out from the storage device 200 makeup parts images, and along therewith reads out guide information correlated with the makeup parts images. Thereafter, in a case where an operation for selecting a makeup parts image is performed by the user while the simulation image is displayed, the image generating unit 103 outputs guide information corresponding to the selected makeup parts image to the display device 300. The display device 300 then displays the guide information. Accordingly, the user can readily comprehend the method and so forth of applying makeup items.

Second Modification

The image processing device 100 may input a facial image indicating a face where makeup has actually been applied following a simulation image on which a makeup parts image has been superimposed, and evaluate the actually-applied makeup by comparing this facial image with the simulation image.

For example, the user actually applies makeup to his/her own face while viewing the simulation image on which the makeup parts image has been superimposed (hereinafter referred to as model image), and photographs the face with a camera. The image input unit 101 then inputs the facial image from the camera (hereinafter referred to as makeup-completed image), and outputs the makeup-completed image to the image analyzing unit 102.

Next, the image analyzing unit 102 extracts regions where makeup has actually been applied (hereinafter referred to as makeup regions) from the makeup-completed image. The image analyzing unit 102 then outputs the makeup-completed image and analysis results information including coordinates and so forth enabling identification of the makeup regions, to the image generating unit 103.

Next, the image generating unit 103 matches the makeup regions indicated in the analysis results information (e.g., regions where cheek color has actually been applied), and makeup parts image superimposing regions included in the model image (e.g., cheek color image superimposing regions). The image generating unit 103 then calculates the proportion of matching between the makeup regions and superimposing regions (hereinafter referred to as evaluation value). The higher the value of the evaluation value is, this indicates that the greater the accuracy of makeup is.

The image generating unit 103 generates information indicating the evaluation value (hereinafter referred to as makeup evaluation information), and outputs to the display device 300. The display device 300 displays the makeup evaluation information. Accordingly, the user can comprehend to what degree the makeup has been accurately performed.

Although an example of a case where the makeup evaluation information is an evaluation value has been described above, this is not restrictive. For example, the makeup evaluation information may be a message, illustration, or the like indicating the accuracy of the makeup, decided base on the evaluation value.

Although an example of a case where the makeup is evaluated by matching the makeup regions and superimposing regions has been described above, this is not restrictive. For example, evaluation of makeup may be performed by matching the color of makeup regions and the color of the makeup parts image. In a case where the results of matching show that there are portions where color difference is a predetermined value of higher (e.g., portions with uneven coloring), the evaluation value may be calculated to be lower. Also, the makeup evaluation information may include information indicating the makeup region with uneven coloring in the form of text, arrows, audio, or the like.

Third Modification

The image processing device 100 may extract skin color from the facial image and select a makeup parts image to be superimposed on the facial image in accordance with that skin color. For example, the image analyzing unit 102 extracts the color of skin regions (e.g., cheek, forehead, chin, etc.) from the facial image. The image analyzing unit 102 then outputs analysis results information including information of the color of skin regions to the image generating unit 103.

The image generating unit 103 reads out makeup parts images (e.g., concealer images, foundation images, etc.) having the same color as the color of the skin regions indicated in the analysis results information, from the storage device 200. The image generating unit 103 then adjusts the shapes and sizes of the makeup parts images to match the superimposing regions, generates a simulation image where the makeup parts images are superimposed on the facial image, and outputs the simulation image to the display device 300. The display device 300 displays this simulation image. Accordingly, the image processing device 100 can propose to the user a makeup parts image suitable for actual skin color.

Although description has been made above regarding an example of a case where the image generating unit 103 selects makeup parts images having the same color as the color of the skin regions, this is not restrictive. For example, the image generating unit 103 may select makeup parts images of approximate colors to the color of the skin regions. For example, an approximate color may be a color that is one or two steps brighter or a color that is one or two steps darker than the color of the skin regions.

Fourth Modification

In a case of having selected one makeup parts image (this may be a makeup parts image specified by the user) to be superimposed on a facial image, the image processing device 100 may select another makeup parts image based on the color of that makeup parts image.

For example, the storage device 200 stores at least one or more makeup parts images correlated with one makeup parts image. This correlation is set beforehand so that the color harmony is achieved among the makeup parts images, based on the Munsell color system, for example. In a case where a foundation image of a predetermined color has been selected as a makeup parts image to be superimposed on a facial image and has been read out from the storage device 200, for example, the image generating unit 103 reads out, from the storage device 200, cheek color images, eye shadow images, and so forth, of predetermined colors correlated with the foundation image. The image generating unit 103 then adjusts the shapes and sizes of these makeup parts images to match the superimposing regions, generates a simulation image where the makeup parts images are superimposed on the facial image, and outputs the simulation image to the display device 300. The display device 300 displays this simulation image. Accordingly, the image processing device 100 can propose multiple makeup parts images, with color harmony achieved, to the user.

Fifth Modification

In a case where a discoloration region is present in a skin region in the facial image, the image processing device 100 may generate a simulation image where a makeup parts image to cover the discoloration region has been superimposed on the facial image. Discoloration regions include pigmented spots, chloasma, nevus spilus, melanocytic nevus, nevus of Ota, acquired dermal melanocytosis, erythema, purpura, vitiligo, bruises, moles, darkening of pores, sunburn areas, acne, acne scars, pigmentation due to friction or inflammation, wrinkles, freckles, tattoos, warts, scarring, and so forth.

For example, the image analyzing unit 102 extracts a region where color difference is a predetermined value or higher as compared with surrounding regions (regions in the skin region around the discoloration region), as a discoloration region. The image analyzing unit 102 then outputs analysis results information including information such as the color of the surrounding regions, coordinates of facial feature points enabling identification of the discoloration region, and so forth, to the image generating unit 103.

The image generating unit 103 reads out a makeup parts image having a color of the surrounding regions indicated in the analysis results information (e.g., for blemish portions such as pigmented spots or the like, a concealer image, foundation image, etc., approximating the skin color or foundation actually applied) from the storage device 200. The image generating unit 103 then adjusts the shapes and sizes of the makeup parts images to match the discoloration region, generates a simulation image where the makeup parts image is superimposed on the facial image, and outputs the simulation image to the display device 300. The display device 300 displays this simulation image. Accordingly, the user can comprehend makeup items of a suitable color to cover discoloration regions.

Sixth Modification

In a case of having received a switching instruction from the user while displaying a simulation image where the facial image is a still image, the image processing device 100 may switch the facial image from the still image to a moving image. Accordingly, the user can visually recognize simulation images of the face tilted to various directions, which makes it further easier to comprehend the colors, shapes, positions, and so forth, of makeup parts images.

Also, in a case of having received a switching instruction from the user while displaying a simulation image where the facial image is a moving image, the image processing device 100 may switch the facial image from the moving image to a still image. Accordingly, the user can take time to visually recognize a simulation image of the face tilted at a predetermined angle, which makes it further easier to comprehend the colors, shapes, positions, and so forth, of makeup parts images.

Seventh Modification

The image processing device 100 may output multiple simulation images to the display device 300, and the display device 300 may display the multiple simulation images side by side. The multiple simulation images being displayed side by side may be of the same type, or may be of different types. For example, a simulation image where a proportion line image has been superimposed on a predetermined facial image (see first operation example), and a simulation image where a proportion line image has been superimposed on a facial image other than the predetermined facial image (see first operation example), may be displayed side by side.

Also, a simulation image where a proportion line image has been superimposed on a predetermined facial image (see first operation example), and a simulation image where a blocking lines image has been superimposed on the same facial image as the predetermined facial image (see third operation example), may be displayed side by side. Accordingly, the user can compare multiple simulation images more readily.

Eighth Modification

The image processing device 100 (e.g., the image generating unit 103, same as above in the present modification) may output only the facial image to the display device 300, and the display device 300 may display just the facial image. Further, in a case where the user has selected a makeup parts image during display of the facial image alone and a superimposing instruction of that makeup parts image has been received, the image processing device 100 may generate a simulation image where the makeup parts image has been superimposed on the facial image being displayed, and output to the display device 300.

Also, in a case of outputting just the facial image, the image processing device 100 may also output a facial image indicating a range over which makeup parts images can be superimposed (hereinafter referred to as superimposable range) to the display device 300. The superimposable range is, for example, out of ranges where a facial image facing forward has been vertically bisected, one of an image of the right half of the face (hereinafter referred to as right face image) and an image of the left half of the face (hereinafter referred to as left face image). For example, in a case where the right face image is the superimposable range, the image processing device 100 generates a facial image where the luminance of the left face image is lower than the luminance of the right face image, and outputs to the display device 300. Thus, the user can recognize that the right face image is the superimposable range.

The student then, for example, selects a desired makeup parts image at a terminal that the image processing device 100 has, and performs operations to instruct the makeup parts image to be superimposed at a desired position in the right face image. On the other hand, the instructor selects a desired makeup parts image at a terminal that the image processing device 100 has (which may be the same terminal that the student is using, or may be a separate terminal), and performs operations to instruct the makeup parts image to be superimposed at a desired position in the left face image. Note that besides the method of selecting a makeup parts image and instructing the superimposing position thereof, the student and instructor may use an electronic pen or the like, for example, to directly draw a makeup parts image on the left face image displayed on the terminal.

Upon having accepted the above-described operations by the student and the instructor, the image processing device 100 generates a simulation image where the makeup parts image selected by the student is superimposed on the right face image (hereinafter referred to as right face simulation image). The image processing device 100 also generates a simulation image where the makeup parts image selected by the instructor is superimposed on the left face image (hereinafter referred to as left face simulation image). The image processing device 100 then outputs the right face simulation image and left face simulation image to the display device 300.

The display device 300 combines the right face simulation image and the left face simulation image to display as a single facial simulation image. At this time, the right face simulation image and the left face simulation image are displayed at the same luminance. Note that the right face simulation image may be displayed with lower luminance than the left face simulation image, or the left face simulation image may be displayed with lower luminance than the right face simulation image. Accordingly, the student can visually recognize the right face simulation image generated by his/her own operations and the left face simulation image generated by operations of the instructor, and can easily compare.

Note that the image processing device 100 may store the right face simulation image and the left face simulation image in the storage device 200 as learning history. Simulation images to be stored in the storage device 200 as learning history are not restricted to right face simulation images and left face simulation image, and may be simulation images of the entire face, for example.

The image processing device 100 may also perform image analysis of multiple right face simulation images stored as learning history, and evaluate tendencies of makeup by the student (e.g., the way that makeup parts images are laid out, color selection of makeup parts images, etc.). The image processing device 100 may output information indicating results of evaluation to the display device 300, and the display device 300 may display this information. Accordingly, the student can comprehend tendencies of his/her own makeup.

The image processing device 100 may also compare the right face simulation image and the left face simulation image, and determine whether the positions, colors, and so forth of makeup parts images that the student has selected agree with the positions, colors, and so forth of makeup parts image that the instructor has selected. The image processing device 100 may also output the results of determination to the display device 300 as determination results information indicated by text, illustrations, audio, or the like. The display device 300 then displays the determination results information. Accordingly, the student can comprehend mistakes and so forth regarding positions, colors, and so forth, of the makeup parts images that he/she has selected.

Ninth Modification

Terminals having the image processing device 100 and display device 300 may communicate with each other. For example, simulation images (e.g., the right face simulation image and left face simulation image described in the eighth modification) may be exchanged between a terminal that the student uses and a terminal that the instructor uses. Accordingly, students residing or staying at remote locations can receive instruction regarding makeup by an instructor.

Also, for example, the instructor creates course data beforehand, indicating the way to proceed with a textbook (e.g., speed of page feed, highlighting of important points, etc.) for remote learning (correspondence learning), and stores the course data in the terminal. The terminal that the student at a remote location uses receives the course data, and displays the textbook based on the course data. Accordingly, remote learning can be performed with a sense of presence, as if the student were actually in class. Note that the instructor may in real time perform operations instructing how to proceed with the textbook, or perform coaching operations regarding a simulation image that the student has created. The terminal that the student uses receives information indicating these operations, and performs display and so forth based on the information.

Tenth Modification

The method of extracting facial feature points and the method of extracting facial parts are not restricted to the description in the above-described embodiment. Known classification methods, pattern recognition methods, clustering methods, and optimization methods may be employed.

Examples of known classification methods include decision tree analysis, neural networks (including deep learning), and naive Bayes. Examples of known pattern recognition methods include neural networks (including deep learning), and support vector machines (SVM). Examples of known clustering methods include k-Nearest Neighbors (k-NN), k-means, and hierarchical clustering. Examples of known optimization methods include genetic algorithms.

Eleventh Modification

Part of the configuration of the image processing device 100 may be physically distanced from other parts of the configuration of the device. In this case, the multiple distanced parts each need to have a communication unit to communicate with each other. For example, part of the functions of the image processing device 100 may be in the Cloud. The image processing device 100 may also include at least one of the storage device 200 and display device 300. The image processing device 100 may also include a device that outputs facial images to the image input unit 101 (e.g., a camera).

For example, in a case where a terminal having the image processing device 100 and display device 300 is connected to a network, created data and operation history may be saved in the Cloud on the network, besides in the terminal. Information collected in the Cloud includes basic facial shapes, facial feature point information, shapes of makeup parts that have been created, history of brush touches and ways of application, information of colors used, information of makeup item products, and so forth. Such information is learned in the Cloud, and trends are analyzed over periods of months or periods of years. Facial shapes and makeup techniques that are trending in that age, such as line shapes, cheek color techniques, and so forth, are analyzed from facial shapes, facial feature point information, shapes of makeup parts, and brush operation history. Popular color usages and product information are extracted from color information and makeup item product information.

Such learning data is accumulated as trending makeup methods and color information, and is automatically downloaded to terminals. The newest makeup information can constantly be referenced and used at the terminals, and guidelines for ways to perform makeup such as illustrated in FIGS. 5A, and 5B, and FIGS. 11A through 12B, for example, are automatically updated to the newest makeup.

An image processing device according to the present disclosure includes: an image input unit that inputs a facial image from a predetermined device; an image analyzing unit that calculates one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image; and an image generating unit that decides a superimposing region of a makeup parts image based on one of the facial shape, the proportion lines, and the blocking lines, and generates a simulation image where the makeup parts image has been superimposed on the superimposing region.

Note that in the image processing device, the image generating unit may calculate an overspread region where the facial shape spreads out from a standard facial shape that has been set beforehand, and an insufficient region where the facial shape does not fill out the standard facial shape, decide a region of the facial image corresponding to the overspreading region to be a superimposing region for a first makeup parts image, and decide a region of the facial image corresponding to the insufficient region to be a superimposing region for a second makeup parts image that is different from the first makeup parts image.

Also, in the image processing device, the image generating unit may calculate luminance of divided regions which the facial image has been divided into by the blocking lines, decide a divided region, where the luminance in the facial image is greater than a first threshold value, to be a superimposing region for a second makeup parts image, and decide a divided region, where the luminance in the facial image is smaller than a second threshold value that is smaller than the first threshold value, to be a superimposing region for a first makeup parts image that is different from the second makeup parts image.

Also, in the image processing device, the first makeup parts image may be a lowlight image, and the second makeup parts image may be a highlight image.

Also, in the image processing device, the image analyzing unit may calculate a first proportion line, a second proportion line below the first proportion line, and a third proportion line below the second proportion line, that divide the facial image in the vertical direction. The image generating unit may decide, in a case where a first distance between the first proportion line and the second proportion line is longer than a second distance between the second proportion line and the third proportion line, a superimposing position of the makeup parts image where the makeup parts image is laid out upwards, and decide, in a case where the second distance is longer than the first distance, a superimposing position of the makeup parts image where the makeup parts image is laid out downwards.

Also, in the image processing device, the image analyzing unit may calculate a fourth proportion line indicating a maximum vertical width of the facial image, and a fifth proportion line indicating a maximum lateral width of the facial image. The image generating unit may decide, in a case where the fourth proportion line is longer than the fifth proportion line, a superimposing position of the makeup parts image where a longitudinal direction of the makeup parts image is laid out following the lateral width of the facial image, and decide, in a case where the fifth proportion line is longer than the fourth proportion line, a superimposing position of the makeup parts image where the makeup parts image is laid out obliquely from a cheek toward a mouth corner.

Also, in the image processing device, the makeup parts image may be a cheek color image.

Also, in the image processing device, the image generating unit may generate the simulation image where an image of the proportion lines is superimposed on the facial image.

Also, in the image processing device, the image generating unit may generate the simulation image where an image of the blocking lines is superimposed on the facial image.

Also, in the image processing device, in a case of having received an instruction to change positions of the proportion lines, the image generating unit may generate a facial image where at least one of the form and position of a facial part in the facial image has been changed based on the positions of the proportion lines after changing.

Also, in the image processing device, the image analyzing unit may calculate at least three or more of the proportion lines. The image generating unit may change, in a case of having received an instruction for idealization of facial balance of the facial image, the positions of the proportion lines to where the distances between the proportion lines are at a ratio decided beforehand, and generate a facial image where at least one of the form and position of a facial part in the facial image has been changed based on the positions of the proportion lines after changing.

Also, in the image processing device, the image generating unit may output the simulation image to a predetermined display device.

An image processing method according to the present disclosure includes: inputting a facial image from a predetermined device; calculating one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image; deciding a superimposing region of a makeup parts image in the facial image, based on one of the facial shape, the proportion lines, and the blocking lines; and generating a simulation image where the makeup parts image has been superimposed on the superimposing region.

An image processing program according to the present disclosure causes a computer to execute processing of inputting a facial image from a predetermined device, processing of calculating one of facial shape, proportion lines that are lines drawn on the face to analyze the balance of the face, and blocking lines that divide the face into multiple regions following the structure of the face according to lightness and darkness of shadows due to light striking the face, based on facial feature points extracted from the facial image, processing of deciding a superimposing region of a makeup parts image in the facial image, based on one of the facial shape, the proportion lines, and the blocking lines, and processing of generating a simulation image where the makeup parts image has been superimposed on the superimposing region.

The image processing device, image processing method, and image processing program according to the present disclosure are useful as an image processing device, image processing method, and image processing program that generate simulation images for makeup.

What is claimed is:

1. An image processing device comprising:
    an image input unit that inputs a facial image from a predetermined device;
    an image analyzer that calculates one of a facial shape, proportion lines that are lines drawn on the face to analyze the balance of the face, and blocking lines that divide the face into multiple regions following the structure of the face according to lightness and darkness of shadows arising due to light striking the face, based on facial feature points extracted from the facial image; and an image generator that determines a superimposing region of a makeup parts image based on one of the facial shape, the proportion lines, and the blocking lines, and generates a simulation image where the makeup parts image has been superimposed on the superimposing region wherein the image generator
- calculates an overspread region where the facial shape spreads out from a standard facial shape that has been set beforehand, and an insufficient region where the facial shape does not fill out the standard facial shape,
- determines a region of the facial image corresponding to the overspreading region to be a superimposing region for a first makeup parts image, and
- determines a region of the facial image corresponding to the insufficient region to be a superimposing region for a second makeup parts image that is different from the first makeup parts image.

2. The image processing device according to claim 1, wherein the first makeup parts image is a lowlight image, and wherein the second makeup parts image is a highlight image.

3. The image processing device according to claim 1, wherein the image analyzer
- calculates a first proportion line, a second proportion line below the first proportion line, and a third proportion line below the second proportion line, that divide the facial image in the vertical direction, and wherein the image generator
- determines, in a case where a first distance between the first proportion line and the second proportion line is longer than a second distance between the second proportion line and the third proportion line, a superimposing position of the makeup parts image where the makeup parts image is laid out upwards, and
- determines, in a case where the second distance is longer than the first distance, a superimposing position of the makeup parts image where the makeup parts image is laid out downwards.

4. The image processing device according to claim 3, wherein the makeup parts image is a cheek color image.

5. The image processing device according to claim 1, wherein the image analyzer
- calculates a fourth proportion line indicating a maximum vertical width of the facial image, and a fifth proportion line indicating a maximum lateral width of the facial image, and wherein the image generator
- determines, in a case where the fourth proportion line is longer than the fifth proportion line, a superimposing position of the makeup parts image where a longitudinal direction of the makeup parts image is laid out following the lateral width of the facial image, and
- determines, in a case where the fifth proportion line is longer than the fourth proportion line, a superimposing position of the makeup parts image where the makeup parts image is laid out obliquely from a cheek toward a mouth corner.

6. The image processing device according to claim 1, wherein the image generator generates the simulation image where an image of the proportion lines is superimposed on the facial image and calculates the proportion lines.

7. The image processing device according to claim 1, wherein the image generator generates the simulation image where an image of the blocking lines is superimposed on the facial image and calculates the blocking lines.

8. The image processing device according to claim 1, wherein, in a case of having received an instruction to change positions of the proportion lines, the image generator generates a facial image where at least one of the form and position of a facial part in the facial image has been changed based on the positions of the proportion lines after changing and calculates the proportion lines.

9. The image processing device according to claim 1, wherein the image analyzer
- calculates at least three or more of the proportion lines, and wherein the image generator
- changes, in a case of having received an instruction for idealization of facial balance of the facial image, the positions of the proportion lines to where the distances between the proportion lines are at a ratio decided beforehand, and
- generates a facial image where at least one of the form and position of a facial part in the facial image has been changed based on the positions of the proportion lines after changing.

10. The image processing device according to claim 1, wherein the image generator outputs the simulation image to a predetermined display device.

11. An image processing method, comprising:
- inputting a facial image from a predetermined device;
- calculating one of a facial shape, proportion lines that are lines drawn on the face to analyze the balance of the face, and blocking lines that divide the face into multiple regions following the structure of the face according to lightness and darkness of shadows arising due to light striking the face, based on facial feature points extracted from the facial image;
- determining a superimposing region of a makeup parts image in the facial image, based on one of the facial shape, the proportion lines, and the blocking lines;
- generating a simulation image where the makeup parts image has been superimposed on the superimposing region;
- calculating an overspread region where the facial shape spreads out from a standard facial shape that has been set beforehand, and an insufficient region where the facial shape does not fill out the standard facial shape;
- determining a region of the facial image corresponding to the overspreading region to be a superimposing region for a first makeup parts image; and
- determining a region of the facial image corresponding to the insufficient region to be a superimposing region for a second makeup parts image that is different from the first makeup parts image.

12. A non-transitory computer-readable recording medium storing an image processing program that causes a computer to execute the operations of
- inputting a facial image from a predetermined device,
- calculating one of a facial shape, proportion lines that are lines drawn on the face to analyze the balance of the face, and blocking lines that divide the face into multiple regions following the structure of the face according to lightness and darkness of shadows arising due to light striking the face, based on facial feature points extracted from the facial image, determining a superimposing region of a makeup parts image in the facial image, based on one of the facial shape, the proportion lines, and the blocking lines, and generating a simulation image where the makeup parts image has been superimposed on the superimposing region, calculating an overspread region where the facial shape spreads out from a standard facial shape that has been set beforehand, and an insufficient region where the facial shape does not fill out the standard facial shape, determining a region of the facial image corresponding to the overspreading region to be a superimposing region for a first makeup parts image, and determining a region of the facial image corresponding to the insufficient region to be a superimposing region for a second makeup parts image that is different from the first makeup parts image.

* * * * *